(12) United States Patent
Greene

(10) Patent No.: US 7,925,519 B2
(45) Date of Patent: Apr. 12, 2011

(54) METHOD AND SYSTEM FOR DELIVERY OF HEALTHCARE SERVICES

(75) Inventor: Jeffrey C. Greene, Norman, OK (US)

(73) Assignee: MedEncentive, LLC, Oklahoma City, OK (US)

( * ) Notice: Subject to any disclaimer, the term of this patent is extended or adjusted under 35 U.S.C. 154(b) by 860 days.

(21) Appl. No.: 11/772,212

(22) Filed: Jun. 30, 2007

(65) Prior Publication Data

US 2008/0033751 A1  Feb. 7, 2008

Related U.S. Application Data

(63) Continuation-in-part of application No. 11/596,305, filed on Dec. 13, 2007, which is a continuation of application No. PCT/US2005/015791, filed on May 6, 2005, which is a continuation of application No. 10/841,240, filed on May 6, 2004, now abandoned.

(51) Int. Cl.
    *G06Q 10/00* (2006.01)
(52) U.S. Cl. .................................... 705/2; 705/3; 705/37
(58) Field of Classification Search .................. 705/2, 3, 705/37
    See application file for complete search history.

(56) References Cited

U.S. PATENT DOCUMENTS

| | | |
|---|---|---|
| 6,161,095 A | 12/2000 | Brown |
| 6,208,973 B1 | 3/2001 | Boyer et al. |
| 6,317,700 B1 | 11/2001 | Bagne |
| 6,558,929 B2 | 5/2003 | Thum et al. |
| 2001/0041992 A1 | 11/2001 | Lewis et al. |
| 2002/0007285 A1 | 1/2002 | Rappaport |
| 2002/0010597 A1 | 1/2002 | Mayer et al. |
| 2002/0072933 A1 | 6/2002 | Vonk et al. |
| 2002/0091546 A1 | 7/2002 | Christakis et al. |
| 2002/0138306 A1 | 9/2002 | Sabovich |
| 2002/0169638 A1 | 11/2002 | Rodriguez-Cue |
| 2002/0169771 A1 | 11/2002 | Melmon et al. |
| 2002/0194022 A1 | 12/2002 | Comite |
| 2002/0194025 A1 | 12/2002 | Notclovitz |
| 2003/0009355 A1 | 1/2003 | Gupta |
| 2003/0135394 A1* | 7/2003 | Padron et al. ............... 705/3 |
| 2003/0163352 A1* | 8/2003 | Surpin et al. ............... 705/2 |
| 2003/0195838 A1* | 10/2003 | Henley ...................... 705/37 |
| 2004/0044546 A1 | 3/2004 | Moore |

* cited by examiner

*Primary Examiner* — Luke Gilligan
*Assistant Examiner* — Valerie Lubin
(74) *Attorney, Agent, or Firm* — Tomlinson Rust McKinstry Grable

(57) ABSTRACT

The current invention is directed to methods for reducing the cost of healthcare by improving the standard of care and by encouraging healthy behavior. Additionally, the methods of the current invention are designed to help improve clinical and economic outcomes through the principles of empowerment and accountability. The methods of the current invention provide financial incentives to both the patient and the medical practitioner in an interactive, web-based incentive system that creates appropriate and powerful checks and balances that motivate medical practitioners and patients to participate and to be adherent to beneficial performance standards. The methods of the current invention achieves the objectives of improved healthiness and better and more affordable healthcare by aligning the interests of medical providers, patients/consumers, and healthcare purchasers/payers in a win-win-win proposition. In the invention, purchasers/payers achieve lower healthcare consumption and costs by compensating medical providers and patients to declare compliance to beneficial performance standards on an intermediary's Internet application, and then having both parties confirm each other's compliance. The methods of the current invention incorporates evidence-based medicine treatment guidelines and content and other performance standards, and dispenses information therapy and other similar types of content through an Internet application or by other means to improve the standard of healthcare treatment and promote healthy behavior, which leads to better clinical outcomes and a reduction in the overall cost of healthcare.

24 Claims, 15 Drawing Sheets http://www.intermediary.com/providerportal.aspx

Web Browser Menu Bar

Intermediary Website Banner

Product Description | News & Press Releases | Providers | Patients | Employers | Administrators Provider Portal

- If you are a first time user click here (to enroll in the Program).
- If you are an enrolled provider please login.

Username [          ]

Password [          ]

[ Login ]

Forgot your username/password? Click here

- If you are a group administrator and need to create a group login click here.

- Instructions
- EBM Content
- Demo Site
- FAQ's

Newsletter and Press Release Content

Web Browser Status Bar

Fig. 4 http://www.intermediary.com/realtime/step1.aspx

Web Browser Menu Bar

Intermediary Website Banner

Product Description | News & Press Releases | Providers | Patients | Employers | Administrators Step 1

Point of Service Initiated Ix Application

This application is designed to offer physicians access to evidence-based medicine guidelines and the ability to prescribe Ix (information therapy) to their patients on a real-time basis. Simply follow the easy five step process beginning with the member (patient) identification number below. Then click the "Continue" link. (If the patient's member identification is not found on their card try their social security number or scroll for their name, below.)

MemberID: [_____]  Continue or

Last Name: [_____]  Continue

For help or to make suggestions Contact Intermediary.

Web Browser Status Bar

Fig. 5 http://www.intermediary.com/realtime/step3.aspx

Web Browser Menu Bar

Intermediary Website Banner

Product Description | News & Press Releases | Providers | Patients | Employers | Administrators Go Back / Log Out

Point of Service Initiated Ix Application*

Step 3

You now need to enter the patient's primary diagnosis followed by any secondary diagnoses You must enter at least the first three digits (alpha-numeric) of the diagnosis code to perform a numeric search.

If you know the numeric code, enter it here: ☐☐☐●☐☐ or

If you need to perform an alphanumeric search, Click Here.

or

Select from a list of your most frequently treated diagnoses, Click Here.

or

Select from a list of this patient's diagnoses, Click Here.

* Real-Time Version
For help or to make suggestions Contact Intermediary.

Web Browser Status Bar

Fig. 6 http://www.intermediary.com/realtime/step3.aspx

Web Browser Menu Bar

Intermediary Website Banner

Product Description | News & Press Releases | Providers | Patients | Employers | Administrators Go Back / Log Out

Point of Service Initiated Ix Application

You have added the following diagnosis.
You may list up to 4 diagnoses by clicking the "Add Another Diagnosis" link, below.
When done selecting diagnoses, click the "Continue to the Next Step" link, below.

Step 3

You may re-order these codes by highlighting a code and clicking the "up-down" arrows Selected Diagnoses Primary Diagnosis:   $1^{st}$ Diagnosis
Secondary Diagnosis: $2^{nd}$ Diagnosis (EBM)
Tertiary Diagnosis:  $3^{rd}$ Diagnosis

[ Up ]
[ Down ]

You may either:
Add Another Diagnosis or Continue to the Next Step

For help or to make suggestions Contact Intermediary.

Web Browser Status Bar

Fig. 7

| http://www.intermediary.com/realtime/step3.aspx |
|---|

| Web Browser Menu Bar | |
|---|---|
| Patient: Test Patient<br>Date of Service:<br>YYYY-MM-DD | Instructions: All questions associated with each diagnosis in the left column must be appropriately answered to the eligible for higher payment on this claim. A "no" response will require a listed or typed explanation. Refer to "No" options under each question. Only the primary diagnosis requires your response, however you can prescribe additional information therapy to your patient by clicking on other listed guidelines and diagnoses. When completed click the "Done" button. Click "Help" for expanded instructions. |
| 1.401.1 (P) BENIGN HYPERTENSION<br><u>Hypertension</u> | <u>Print Guideline</u><br>Hypertension Decision Tree |
| Are you following this guideline for this patient?<br>☐ Yes<br>☐ No<br><u>Click here for "no" options</u> | <u>Hypertensive Crisis?</u> → No<br>If not Hypertensive Crisis Begin <u>Lifestyle Modification:</u> Lose weight, limit alcohol, increase activity, reduce sodium, maintain potassium, calcium, and magnesium, stop smoking, reduce saturated fat, and cholesterol. |
| Do you wish to prescribe information therapy to this patient?<br>☐ Yes<br>☐ No<br><u>Click here for "no" options</u> | Not at Goal BP<br>Initial Drug Choices<br><u>Specific Indications</u>   Uncomplicated<br>Diuretics<br>Beta-Blockers |
| Please rate your patient's compliance for this diagnosis.<br>☐ Complaint<br>☐ Compliance is a non-factor<br>☐ No Response | ACE inhibitors Angiotension II Receptor blockers Alpha-blockers Alpha-beta-blockers Beta-blockers calcium antagonists Diuretics |
| [ Help ]  [ Done ] | |

Fig. 8 http://www.intermediary.com/realtime/step3.aspx

Web Browser Menu Bar

| Patient: Test Patient Date of Service: YYYY-MM-DD | Instructions: All questions associated with each diagnosis in the left column must be appropriately answered to the eligible for higher payment on this claim. A "no" response will require a listed or typed explanation. Refer to "No" options under each question. Only the primary diagnosis requires your response, however you can prescribe additional information therapy to your patient by clicking on other listed guidelines and diagnoses. When completed click the "Done" button. Click "Help" for expanded instructions. |
|---|---|
| 2.401.1 (P) BENIGN HYPERTENSION <u>Hypertension</u> | <u>Print Guideline</u>     Hypertension Decision Tree |

Are you following this guideline for this patient?
- ☐ Y
- ☒ N

<u>Click here for options</u>

Close
- <u>Co-morbidity</u>
- <u>Emergent Condition</u>
- <u>Pending Lab or other test Result</u>
- <u>Contraindicated because;</u>
- <u>Patient declines for financial reasons</u>
- <u>Patient declines for other reasons:</u>

Begin Lifestyle alcohol, increase potassium calcium uce saturated fat

Do you wish prescribe inf tion therapy patient?
- ☐ Yes
- ☐ No

<u>Click here for "no" options</u>

Please rate your patient's compliance for this diagnosis.
- ☐ Complaint
- ☐ Compliance is a non-factor
- ☐ No Response

[ Help ] [ Done ]

Hypertensive Crisis?

Initial Drug Choices

Specific Indications     Uncomplicated

Diuretics Beta-Blockers

ACE inhibitors Angiotension II Receptor blockers Alpha-blockers Alpha-beta-blockers Beta-blockers calcium antagonists Diuretics

Fig. 9

1st Diagnosis – Web Browser Information Bar

Step 2 of 6

Review medical information related to this diagnosis and answer the questions at the bottom of each section.

High Blood Pressure – Description

WHAT IS HYPERTENSION?

Hypertension or high blood pressure is a serious disease that affects nearly 50 million Americans. It causes stroke, heart attack, heart failure, kidney failure, and premature death and disability. It can also cause damage to the eyes and blood vessels. The best way to find high blood pressure is to measure the pressure in the left or right arm. Measuring the blood pressure is important. Once the disease is found, it can be treated with drugs or lifestyle changes.

Blood pressure is simply the pressure within the blood vessels associated with each heartbeat.

401.9/Hypertension NOS

Key Points
Description
Causes
Symptoms
Diagnosis
Prevention & Treatment
Alternative Therapy
Prognosis

Fig. 11 ePPO Claim Wizard Final Questionnaire – Web Browser Information Bar

Step 4 of 6

Please complete the Following Final Questionnaire (page 1)

1. Did your doctor direct you to this website and discuss the reasons why you should view this information?
   O Yes  O No 2. Did you doctor prescribe medication to you?
   O Yes  O No 3. Are you taking your medications?
   O Yes  O No 4. How are you tolerating your medications?
   O Not Well at All   O Not Very Well   O Well   O Very Well

Fig. 12 http://demo.eppopatient.com – Reward Page – Web Browser Information Bar

Step 5 of 5

Confirmation Document          Print / Close

Test Company

Date

Intermediary Participation Confirmation

Congratulations on completing the information therapy process. Your active participation in the Intermediary Program has earned you a financial reward. Your employer / payer has been notified of your participation and you should receive your financial reward by mail in the near future. You may print this document for your records.

Fig. 13

METHOD AND SYSTEM FOR DELIVERY OF HEALTHCARE SERVICES

CROSS REFERENCE TO RELATED APPLICATIONS

This application is a continuation-in-part of U.S. patent application Ser. No. 11/596,305, filed Dec. 13, 2007, which is a continuation of PCT Patent Application No. PCT/US05/15791, filed May. 6, 2005, which is a continuation of U.S. patent application Ser. No. 10/841,240, filed May. 6, 2004 now abandoned, the contents of which are incorporated fully herein by reference.

BACKGROUND OF THE INVENTION

Currently, the healthcare industry represents 15% of the country's GNP. Americans spend considerably more than citizens of any other developed country on healthcare and yet Americans' life expectancy and infant mortality rates rank toward the bottom of these countries. A growing number of Americans are losing their health insurance because it is becoming increasingly unaffordable. Current estimates place the number of uninsured at 45,000,000 to 47,000,000. The supply of physicians is becoming an increasingly critical problem. The United States ranks $43^{rd}$ in the world in the number of physicians per capita just as the "baby-boomer" generation begins to reach retirement age. Most experts have declared the current healthcare delivery system as unsustainable. The present invention is directed to a method and web-based system for improving the delivery of healthcare related services by increasing communication between the service providers and patients, increasing the amount of knowledge a patient has about his or her health condition, providing a system of "checks and balances" to measure and motivate patient and service provider adherence to an accepted performance standard, and providing performance-based rewards to the service provider and patient for their participation in the system.

Since the mid-1980s, several attempts have been made to control healthcare costs. The attempted reforms only temporarily slowed the escalation of healthcare costs during the mid to late 1990s. Recently healthcare costs have risen at an alarming rate—three to four times the rate of inflation during the time period from 2001 through 2006. Control of healthcare costs can be accomplished by elevating the efficiency and effectiveness of the standard of care and by improving the country's overall level of healthiness.

Various studies have concluded that healthcare costs are increasing for the following reasons:

High Cost Coupled with Poor Healthcare Quality Equates to Low Value—Healthcare in the United States is more expensive than any other developed country and life expectancy and infant mortality in the United States ranks toward the bottom of developed countries. A study by the RAND Corporation determined that Americans receive recommended care only 55% of the time. (See McGlynn E A. *The Quality of Healthcare Delivered to Adults in the United States.* RAND Corporation.) This low level of healthcare causes inferior clinical outcomes and higher costs.

Variability of Care—Another cause of poor quality of care is the variability of care from provider to provider and from geographic location to location. (See Wennberg J., *Small Variations in Healthcare Delivery, and Understanding Geographic Variations in Healthcare Delivery* and Dartmouth Atlas of Healthcare 1998.) Variability in healthcare indicates a degree of over-treatment, under-treatment and mistreatment that contributes to inferior clinical outcomes and higher cost.

Hospital Medical Errors—The fourth leading cause of preventable death is due to errors committed in hospitals, accounting for as many a 195,000 deaths per year. (See HealthGrades, *Patient Safety in American Hospitals*, 2004.) This is a tragic situation in terms of human loss. Beyond the human toll, the economic impact of hospital errors on victims and survivors is enormous.

A Large and Growing Population of Uninsured—47 million Americans are without health insurance coverage, and this number continues to grow as coverage becomes increasingly unaffordable.

Poor Doctor-Patient Communications—Studies have documented that a leading complaint about healthcare among patients is the poor communications with their doctors. Doctors interrupt patients within the first twenty-three (23) seconds of an encounter. (See Beckman H B. *The Effect of Physician Behavior on the Collection of Data.*) Fifteen percent (15%) of patients fully understand what their doctors tell them and fifty percent (50%) leave their doctors' offices uncertain of how to care for themselves. (See Kaplan S H, *Is Your Doctor Really Listening to You?*, University of California, Irving, National Center for Policy Analysis. Daily Policy Digest; 2004 citing Levine M. *Tell the Doctor All Your Problems, but Keep It to Less Than a Minute.*) Poor doctor-patient communications causes misdiagnosis, inferior clinical outcomes, malpractice, and higher costs. (See Stewart M A., *Effective Physician-Patient Communication and Health Outcomes: A Review*; and Levinson W., *Physician-patient Communication. The Relationship with Malpractice Claims among Primary Care Physicians and Surgeons.*)

Lack of Patient Medical Knowledge—Most patients do not understand their medical condition well enough to effectively self-manage their health. As a result, patients either become too dependent on their doctors for managing their health or they do not seek healthcare until it is too late. In either case, the cost of healthcare is negatively impacted.

Misaligned Provider and Patient Incentives—There are six incentive misalignments that are characteristic of the American healthcare delivery system that drive costs higher. First, the primary method for compensating providers, especially physicians, is based on the volume of services rendered as opposed to the quality or value of services rendered. This volume-based method of reimbursement encourages physicians and hospitals to provide more care as opposed to better care. Second, American medical providers are primarily compensated to treat illness and injury. They are compensated very little to prevent disease and injury, and are not compensated at all to cure patients or for elevating healthiness. Third, American healthcare is one of the only industries or professions where providers routinely get paid to fix their mistakes. Fourth, providers practice what is referred to as "defensive medicine" to avoid medical malpractice lawsuits. In so doing, doctors perform procedures and order tests that may provide lawsuit protection but have been determined by evidence-based medicine to be unnecessary for the health of the patient. Research has concluded that defensive medicine increases healthcare cost by 5% to 9%. (See Kessler D., *Do Doctors Practice Defense Medicine?*) The fifth misalignment involves how most health insurance plans induce patients to behave. When patients have little or no out-of-pocket costs, a degree of entitlement occurs. Furthermore, health benefits do not reward patients for healthy behaviors or compliance to care recommendations. The sixth misaligned incentive is how pharmaceutical companies market to consumers and pander to physicians to sell brand name drugs when generic or substitute drugs are just as effective. All six of these incentive misalignments stimulate healthcare inflation because these misalignments discourage patients and healthcare service provider accountability and do not empower the parties to improve health or control costs.

A Disparity between Who Controls Healthcare Costs and who is compensated for Delivering Healthcare Affects Healthcare Inflation—Medical practitioners (physicians) and patients (consumers) control the vast majority of cost (approximately 80%). In effect, physicians are the only party licensed to admit and discharge people in and out of a hospital, and are, effectively, the only party licensed to write drug prescriptions and other types of therapies and diagnostic services. Patients are the only party that can choose to follow recommended treatments and adopt healthy lifestyles—a factor that drives the vast majority of healthcare consumption. The epidemic state of obesity and diabetes are recent phenomenon directly related to such lifestyle choices. Therefore, physicians and patients control the vast majority of healthcare consumption, and yet physicians receive less of the premium dollar (19%) than pharmacy (22%), administration and underwriting (250%) and hospitals (28%).

Unhealthy Behaviors—Americans are increasingly unhealthy with preventable diseases such as obesity and diabetes reaching near epidemic rates. This is a primary cause of healthcare inflation.

American Healthcare Delivery is Inefficient—According to a Boston University study, inefficiencies in the American healthcare delivery system may account for 50% of the total cost of healthcare.

Slow Adoption of Medical Advancements—The delay in full adoption, seventeen years in some cases, of advancements in medicine by the medical profession is a contributor to inferior health care that can lead to higher total and long term costs.

Additional studies and the consensus of opinion have concluded the following:

When the standard or quality of healthcare improves then clinical outcomes improve and overall costs are reduced. Thus, the efficacy of a healthcare quality improvement program can be measured by cost trends.

Evidence-based medicine (EBM) treatments represent the highest standard of care. The term EBM, as used herein, means " . . . the conscientious, explicit, and judicious use of current best evidence in making decisions about the care of individual patients. The practice of evidence based medicine means integrating individual clinical expertise with the best available external clinical evidence from systematic research." (Sackett D L, Rosenberg W M C, Gray J A M, Haynes R B, Richardson W S., *Evidence Based Medicine: What It Is and What It Isn't*. BMJ 1996; 312: 71-2.) The consensus of expert opinion holds that EBM must be an integral part of any serious solution to improving the health care delivery system.

Americans would prefer that their healthcare providers be compensated on the basis of value as opposed to volume. (Blue Cross and Blue Shield Association of America.)

Incentive-based ("pay-for-performance" or "P4P") programs have demonstrated that providers can be motivated to report quality measurements. These programs have also demonstrated improvements in the standard of care and clinical outcomes. However, no P4P program has been able to demonstrate sustainable cost containment that produces a return on investment (ROI) for the purchaser, to date. ("Efficiency" is another term used to describe a P4P program that is able achieve simultaneous health care quality improvement and cost containment.)

Physicians find incentive-based programs that mandate adherence to guidelines treatment protocols as objectionable. Many medical practitioners consider these types of P4P programs as "cookbook medicine", counterproductive, potentially dangerous, and will be rejected by the medical community. (American Medical Association)

Information therapy (Ix) changes patient behavior, improves clinical outcomes, and lowers costs. (Blue Cross and Blue Shield Association of America and RAND Corp) As used herein, Ix is defined as dispensing the right clinical information, at the right time, so the patient can make the right decision about the management of their health. Proponents of Ix agree that it is powerful medicine. (Center of Information Therapy). Another way of describing Ix and its importance is to recognize and acknowledge that an uninformed or misinformed patient will have worse clinical outcomes and consume more healthcare resources than a patient that is medically literate. Information therapy provides a means for reducing medical illiteracy.

Electronic health records (EHRs) and personal health records (PHRs) will allow the sharing of patient medical records between service providers. Sharing of patient medical records improves the efficiency and effectiveness of healthcare delivery and adds to patient safety. However, service providers and consumers/patients have been slow to adopt EHRs and PHRs because the value proposition for adoption has been inadequate, to date. In other words, the financial and other incentives have not been sufficient for the vast majority of medical practitioners and consumers to invest the time and money to adopt EHRs and PHRs.

Electronic order entry allows the service provider to prescribe drugs and refer patients to a specialist or other healthcare providers more efficiently and effectively. Electronic order entry of pharmacy prevents errors due to a doctor's illegible hand writing and due to multiple parties handling drug a single prescription. It also provides a means through the Internet to: 1) automate the use of drug formularies that suggest equally effective yet less expensive alternative drugs including generic drugs to doctors, pharmacists and patients; 2) warn doctors and patient of possible harmful drug interactions; and provide the doctor and patient with pharmacy educational information. (This type of electronic order entry can also be referred to as drug therapy management.) Electronic order entry of patient referrals eliminates the time and expense involved in doctor offices or patients calling other doctor offices to for appointments. It also provides a means to forward patient medical information electronically which can significantly improve the efficiency of care and prevent errors and miscommunications. Electronic referrals also helps ensure that the patient makes and keeps an appointment with a specialist.

Pre-authorization certification (pre-cert programs) of expensive medical services (such as surgeries, hospitalizations, and radiological tests like MRIs) has been a long stand practice in health care. In effect, medical providers are required by health plans (healthcare purchasers/payers/funders) to have expensive medical service approved by a third party medical expert to prevent unnecessary services. Typically, patients are not expected or required to be part of the decision-making process.

Comprehensive hospital care management is designed to help insure patients receive the safest and most effective care during a hospitalization. The Institute of Medicine (IOM) offers a list of suggestions for patient safety during hospitalization such as insisting caregiver wash their hands to prevent infection, changing bed linens and turning patients to prevent bed sores and having patients designate advocates (family and friends) to watch over them during hospitalizations. Typically, patients and their advocates are not expected or required to be part of the hospital care management.

According to experts, the success of incentive-based (P4P) programs will hinge on:
  Service provider and patient acceptance, participation and compliance with performance standards that improve the standard of care and level of healthiness that lead to better clinical outcomes and lower overall costs;
  Incorporation of performance standards that have been effective such as EBM, Ix, EHRs, PHRs, electronic order entry, drug therapy management, and hospital care plans;
  Investment in quality improvements to achieve cost control;
  Effective control of fraud and abuse;
  The cost and complexity of deploying and maintaining incentive-based programs; and
  The return on investment to the healthcare purchaser/payer.

All of these factors contribute to the quality and cost of healthcare and will determine the success of P4P programs.

The current invention is directed to improving the delivery of healthcare and the maintenance of good health by creating a system of incentives that align the interests of healthcare's essential stakeholders—healthcare service providers (principally physicians and hospitals), consumer/patients, and purchasers/payers (health insurers, self-insured employers, and the government's Medicare and Medicaid programs). Other quality improvement and cost containment methods consistently fail to recognize or accommodate for this fundamental success criterion of stakeholder alignment. Therefore, the challenge to reforming healthcare has been creating a solution that offered a simultaneous win-win-win proposition among these key stakeholders. The present invention provides an effective system to lower healthcare costs by "triangulating" the interests of the provider, the patient and the purchaser to improve the standard of care and encourage healthy behaviors that leads to better health.

SUMMARY OF THE INVENTION

The present invention is directed to a method for managing delivery of healthcare services. The method comprises receiving a diagnosed health condition of a patient and a claim for services rendered from the service provider. A performance standard is sent to a service provider based on the received diagnosed health condition. The service provider is queried to generate a service provider declaration of adherence or a reason for non-adherence to the performance standard. The diagnosed health condition, the performance standard, and the declaration of adherence or the reason for non-adherence are transmitted to the patient. The patient is queried to generate a patient demonstration of knowledge of the diagnosed health condition and a declaration of patient adherence or reason for non-adherence to the performance standard. The patient demonstration of knowledge, the declaration of patient adherence or reason for non-adherence is transmitted to the service provider. The service provider is queried to generate a service provider confirmation of the patient demonstration of knowledge, the declaration of patient adherence, or the reason for non-adherence to the performance standard. The patient is queried to generate a patient confirmation of the service provider declaration of adherence or reason for non-adherence to the performance standard. The service provider confirmation, the patient confirmation, the service provider declaration of adherence or reason for non-adherence, and the patient demonstration of knowledge, patient declaration of adherence or reason for non-adherence are authenticated and payment of the claim for services rendered and disbursement of a performance-based incentive to the service provider and a performance-based incentive to the service provider are authorized based on authentication.

The present invention is further directed to a web-based method for managing healthcare delivery. The method comprises receiving a patient identification and at least one diagnosis from a service provider through a web interface. The method further includes transmitting a performance standard to the service provider corresponding with each diagnosis received from the service provider through the web interface. A service provider declaration of adherence to the performance standard or a reason for non-adherence is received from the service provider. An information therapy prescription and a rating of patient adherence to the performance standard are received from the service provider. Authorization from the service provider to allow the patient to verify the service provider declaration of adherence to the performance guideline or to express an opinion about the reason for non-adherence and to have the service provider declaration of adherence to the performance standard or the reason for non-adherence that authenticated and adjudicated. Disbursement of a performance-based incentive to the service provider based upon verification by the patient and authentication and adjudication of the service provider declaration of adherence or the reason for non-adherence to the performance standard is occurs upon receipt of verification by patient.

The present invention further includes a system for managing healthcare delivery. The system comprises a healthcare services provider web-based interface, a patient web-based interface, and a means to automatically authenticating and adjudicating. The healthcare services provider web-based interface is adapted to accept a patient identification and a diagnosis from a healthcare services provider, to transmit a performance standard and an information therapy to the healthcare services provider based upon the diagnosis, to accept a healthcare service provider declaration of adherence or reason for non-adherence to the performance standard, to accept a healthcare service provider rating of patient adherence to the performance standard, to accept a healthcare service provider information therapy prescription to the patient, and to accept healthcare service provider verification of a patient declaration of adherence to the performance standard. The patient web-based interface is adapted to provide the patient with the performance standard and the information therapy prescription, to provide at least one query to the patient regarding the information therapy and the performance standard, to receive at least one answer to the at least one query, to accept the patient declaration of adherence, to accept a patient verification of the service provider declaration of adherence. The means for automatically adjudicating and authenticating the service provider declaration of adherence, the patient declaration of adherence, the patient verification of the healthcare service provider declaration of adherence, and the healthcare service provider verification of the patient declaration of adherence; for providing an authorization for disbursement of a performance-based reward to the patient and a performance-based reward to the services provider upon adjudication and authentication.

BRIEF DESCRIPTION OF THE FIGURES

FIG. 4 is an illustrative representation of a webpage used in the method and system of the present invention.

FIG. 5 is an illustrative representation of a webpage used in the method of the present invention. The webpage shown represents a step in the method of accepting a patient's member ID or last name.

FIG. 6 is a representative webpage interface used to accept a diagnosis from a service provider.

FIG. 7 is an illustrative webpage interface that may be used in the present invention. The webpage of FIG. 7 is adapted to accept multiple diagnoses from a service provider, if necessary.

FIG. 8 is a webpage interface designed to guide the service provider through the performance-based standards for a selected diagnosis.

FIG. 9 is an exemplary webpage of the present invention illustrating the interactive nature of the present invention by showing a menu of reasons for non-adherence upon deviation from the performance standard.

FIG. 11 is an internet webpage used to provide the patient with health information about his/her diagnosis including EBM treatments, recommended care, health maintenance, and/or other performance standards.

FIG. 12 illustrates and exemplary webpage comprising a questionnaire used to allow the patient to indicate his/her knowledge or understanding of the health information provided by the webpage shown in FIG. 11.

FIG. 13 is an exemplary voucher used to notify the patient they have completed the information therapy process and earned a financial reward.

DESCRIPTION OF THE PREFERRED EMBODIMENTS

Figure 1:
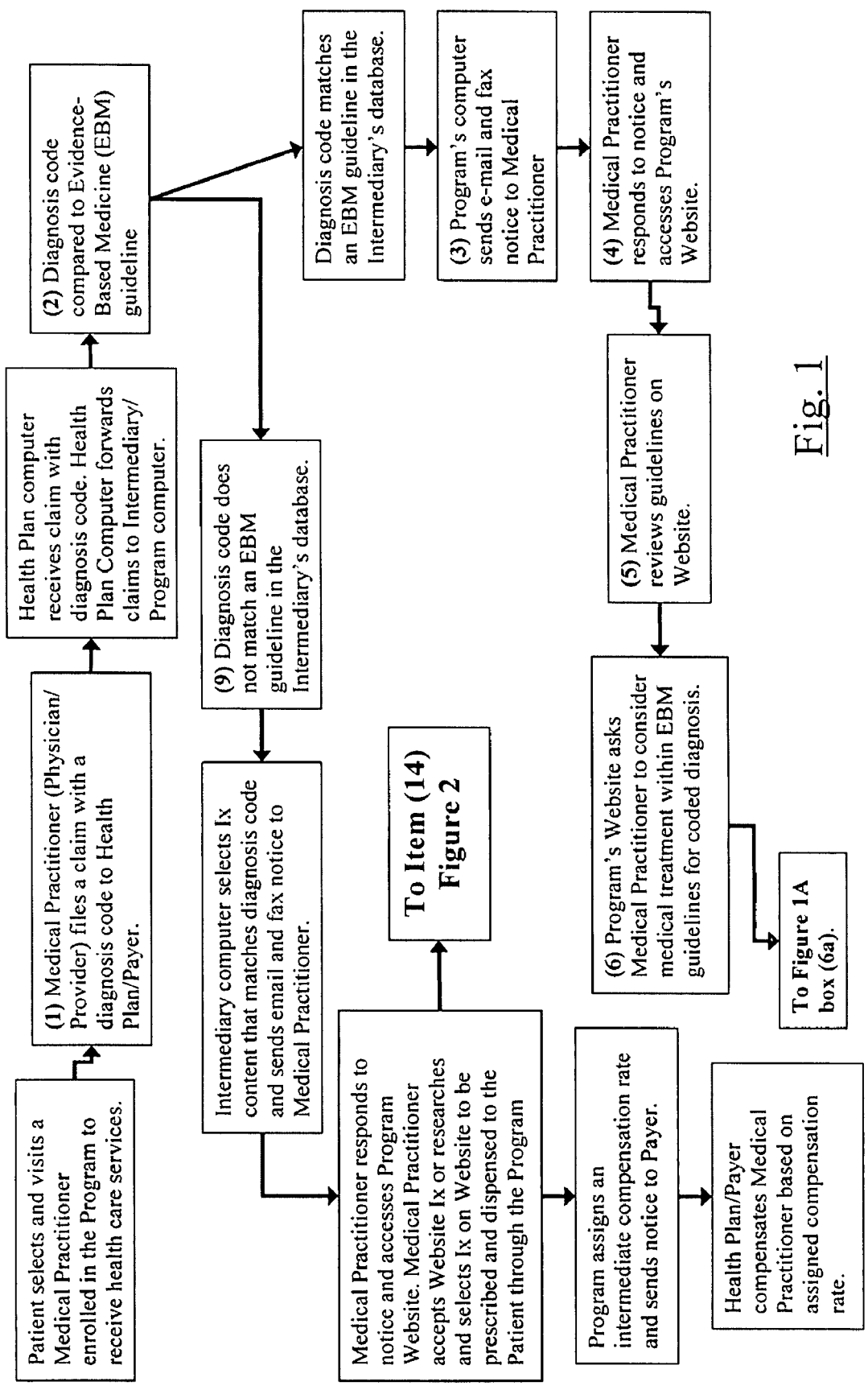
FIG. 1 is a flow chart representing the medical practitioner's portion of one embodiment of the Program.
Figure 1A:
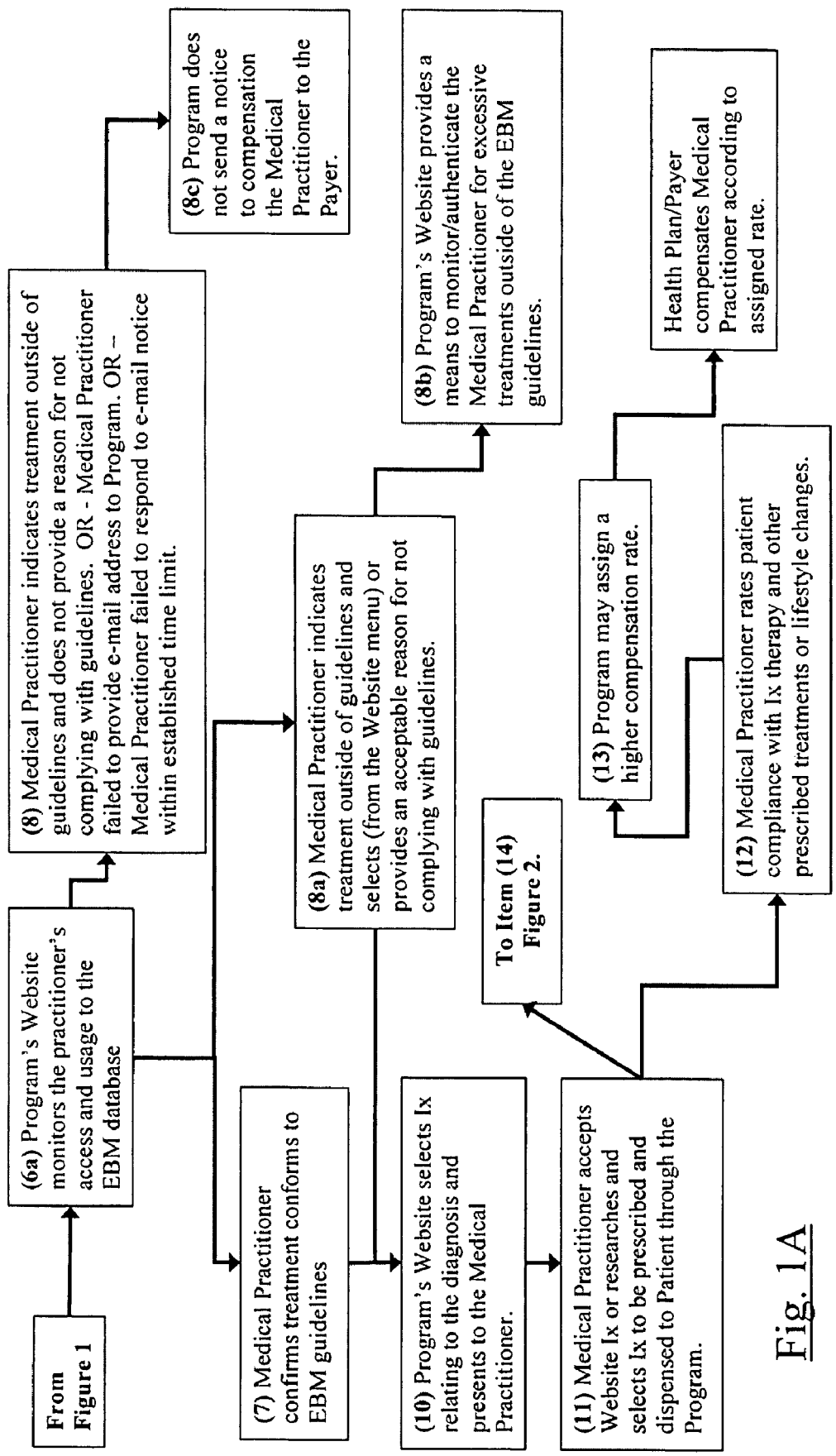

The current invention is often referred to as a healthcare "pay-for-performance" or "P4P" program. Most P4P programs exclusively reward or motivate medical providers (doctors and hospitals). The current invention rewards both the medical provider and the patient "interactively" in a manner that creates a simultaneous benefit to the service provider, the patient, and the purchaser/payer (health plan). The current invention may preferably be described as an "alignment of interest" or "AOI" program because it aligns the interest of the medical provider, patient and purchaser/payer in a "win-win-win" proposition.

The current invention typically involves four (4) parties: the medical provider or practitioner (doctors and/or hospi-
tals); the patient (consumer or health plan member); the party who underwrites the cost or risk of the healthcare (purchaser or payer or employer or insurer or government or health plan); and the independent operator of the invention (referred to as an intermediary or "Informediary")

The current invention also comprises the following elements: a performance standard (or set of performance standards) that have been shown (preferably by a independent and credible third party) to be effective at improving health and controlling healthcare costs; performance-based incentives that may comprise financial rewards paid by the health plan to the medical provider and patient; a system of checks and balances that asks the medical provider and the patient to independently and individually declare adherence to the performance standard and further asks the service provider and patient to independently and individually confirm each other's declaration of compliance; and a website (Website) operated by the Informediary that comprises a set of proprietary Internet applications that facilitates the system of checks and balances.

In the current invention, the health plan disburses performance-based rewards to the medical provider and patient when the Informediary authenticates that the medical provider and the patient have accessed the Website, demonstrated or gained knowledge about the performance standard, declared adherence to the performance standard, and confirmed (or denied) the adherence to the performance standard by the other party.

The current invention is designed to "bolt on" to health plans (including plans sponsored by health insurers, the government's Medicare and Medicaid programs, and self-insured employers) to improve healthcare and increase affordability. Accordingly, health plans are potential customers of the current invention. The $I_x$ Program provided by the current invention directs the health plan to financially reward service providers (medical practitioners) and patients "interactively" for controlling healthcare costs and utilization through the incorporation of evidence-based medicine treatment guidelines, information therapy, and healthy behaviors, which are collectively referred to as performance standards of the Ix Program. The current invention is delivered through a proprietary Internet Website where doctors: and patients read pertinent medical content and respond to a series of questions to determine and confirm compliance to performance standards that have been shown to improve the standard of care and the level of health, which in turn, lead to lower healthcare costs. The invention is intended to compliment other quality improvement and cost containment methods such as disease management; consumer-driven healthcare; population health management including health risk assessment, health screenings, wellness examinations, wellness programs, smoking cessation, predictive modeling; medical malpractice risk management; personal health records, recommended hospital care management programs; pre-authorization certification of expensive procedures and tests; pharmacy benefit management including electronic prescribing, therapeutic substitutions, and drug interaction; electronic health monitoring devices; and electronic health (medical) records.

Rewarding medical practitioners (physicians and hospitals) in this fashion is commonly referred to as "pay-for-performance" or "P4P." It is also referred to as "value-based" healthcare, in contrast to "volume-based" healthcare. However, the current invention's incentive system is unlike any other P4P program in that financial rewards are paid by the health plan (healthcare purchaser/payer) to both the medical provider (practitioner) and the patient for voluntarily, individually and independently (or dependently) declaring (or demonstrating) compliance to performance standards (that are known to improve health and reduce utilization and cost of health services) through the invention's Website, and also for agreeing to allow the other party to individually and independently confirm (verify or acknowledge) each other's declaration (or demonstration) of performance through the Website. In effect, the health plan (healthcare purchase/payer) financially rewards the medical practitioner and the patient to voluntarily serve as each other's "judge and jury" as to each other's adherence to beneficial performance standards. Since the invention is accomplished through a proprietary Internet Website that allows for an independent third party or a health plan to authenticate and report the medical practitioner and patient's "declarations and confirmations", a natural check and balance is created that serves as a very effective and efficient means (incentive) to shape the behaviors of the medical practitioner (provider) and the patient, which is above and beyond the invention's financial rewards. This process of "declare and confirm" and "demonstrate and acknowledge" create "checks and balances" that defines the term "interactive" rewards and incentives. In the present invention, the interests of the medical practitioner (provider), the patient and the health plan (purchaser/payer) in a win-win-win proposition are aligned. More specifically, medical practitioners are rewarded with more compensation for rendering a higher standard of care that offers several other important benefits to the medical practitioner. Patients earn financial rewards for demonstrating knowledge of and compliance to healthy behaviors and rating their medical practitioner's performance, while gaining knowledge to self-management their health and the peace of mind that their medical practitioners are rendering recommended EBM care. Health plans (healthcare purchasers/payers) gain a means to insure that they are receiving greater value for their healthcare payments, plus a means to adjust both the size and nature of the rewards and performance standards to achieve better healthcare, healthiness and cost containment. Because of its unique aligning feature, the invention could be described as an "alignment of interest" or "AOI" program as opposed to a P4P program.

The current invention provides an $I_x$ (Ix) Program model that rewards service providers (medical practitioners) financially and in other ways when they adhere to a performance standard such as considering an EBM treatment guideline and prescribing $I_x$ to their patients through a medical practitioner Internet Website application. The rewards, however, may comprise financial rewards or other rewards limited in their type and nature by the imagination of the health plan (healthcare purchaser/payer) customer of the current invention. The same holds true for performance standards. In addition to EBM treatment guidelines and Ix prescriptions, a medical practitioner performance standard could also be any service independently judged and validated to be beneficial to the patient that can be structured interactively through the invention's Website. Examples of these types of performance standards include: patient-integrated pre-authorization certification of expensive medical services; patient-integrated hospital care management systems; drug therapy (pharmacy benefit) management programs including e-prescription, therapeutic drug substitution, automated drug interactions, and patient education verification; the adoption and use of personal health records; medical education programs; wellness and fitness programs; compliance to recommended treatments; use of automatic health monitoring devices; and adoption of health self-management programs. In effect, the health plan can choose a specific health objective, such as prenatal care with self-management testing that is confirmed by a licensed obstetrician (who is compensated for the extra time and liability). Then the health plan can specify an extra amount of financial rewards, such as $200 for patient performance against this performance standard, whereas a normal patient financial reward may be $25. The health plan's objective is to prevent health problems for the mother and child, and the associated costs. This process illustrates just one of countless ways a health plan can use the invention to target a specific health or cost objective. It is referred to a "precision-guided rewards and performance standards."

In the Ix program model of the current invention, the process of a doctor (service provider) accessing the Website to "practice the method" (Ix Program or Program) by considering EBM and prescribing Ix can be initiated as a result of the doctor's normal insurance claim filing. The receipt of a claim for an applicable service, such as a patient office visit, prompts the independent intermediary to send an email or fax notification to the doctor. This notification directs the doctor to access the Website to "practice the Program." In this example, when the doctor successfully responds to the Website, the independent intermediary notifies the health plan to compensate the doctor for practicing the Program for the associated patient office visit. This implies that the method facilitates timely and direct physician (service provider) compensation for each patient encounter on a per-occurrence-of-care basis. This method of compensation is considered "Pavlovian" in that physicians receive quick rewards that are directly tied to their performance. Other incentive-based (P4P) programs that compensate physicians in an indirect and untimely fashion, such as annual payments, are often based on formulas designed to measure a variety of performance criteria and judged by a third party. Physicians find these types of incentive-based programs objectionable, especially when compensation is based on complicated formulas or dependent on patient performance or involve "cookbook medicine" or judge by third parties that physicians do not trust. In a preferred embodiment of the current invention, doctors can initiate the process during the patient office visit on a "real-time" basis through the medical practitioner (service provider) Internet Website applications. The doctor's appropriate responses entered into the Website affect an immediate information therapy prescription to the patient. The doctor's responses are stored in the independent intermediary's Website database. When the doctor files an insurance claim for an applicable medical practitioner service (such as a patient office visit), the claim 1s forwarded (typically through the health plan's administrator by electronic means) to the independent intermediary. The claim 1s then linked to the doctor's stored Website responses. The independent intermediary then notifies the health plan to compensate the doctor for practicing the program for the associated patient office visit.

As described earlier, the current invention can also be initiated "after-that-fact" when the independent intermediary identifies applicable medical practitioner services from the filing of a claim for reimbursement. This triggers an e-mail notification from the independent intermediary to the medical practitioner (doctor). The doctor responds to the e-mail through the medical practitioner Website. The medical practitioner's appropriate responses can affect an automatic payment or reimbursement increase to the medical practitioner (for practicing the Program) and an information therapy prescription to the patient.

When the patient receives the Ix prescription by mail or e-mail (or handed to the patient during the encounter by the doctor), he/she is directed to a patient Website. There the patient is asked to read evidence-based medical content and answer a series of questions These questions are designed to test the patient's understanding of his/her condition, the recommended treatments, and how best to self-manage his/her condition. These questions also determine the patient's adherence to recommended treatment, and seek his/her impression of the doctor's care relative to recommended care (treatments). As the patient answers these questions, the patient scores points toward a financial reward or rebate of the patient's out-of-pocket medical expenses. The patient's score is automatically forwarded by the independent intermediary to the patient's health plan which affects the disbursement of a performance-based reward. In an alternative embodiment of this model of the invention, the independent intermediary can disburse the performance-based rewards to doctors and patients from funds supplied by the health plan. The current invention provides for the automatic or optional forwarding of the patient's actual responses by the independent intermediary through the Website to the patient's doctor to support subsequent care and as a means for the doctor to confirm the patient's declaration of adherence to a performance standard.

The current invention has a number of built-in features that are designed to achieve service provider and patient acceptance to produce better care and healthy behaviors while controlling costs. One of these features addresses concerns doctors have about being forced to practice "cookbook medicine." The current invention allows and, in fact, encourages service providers (medical practitioners) to deviate from treatment guidelines when it is appropriate in their judgment. The medical practitioner Website offers the doctor a menu of reasons to deviate or the doctor can briefly describe a reason. The doctor is eligible to be paid at the highest available rate if they indicate their adherence to or their reason for deviation from or non-adherence to a guideline. If the doctor provides a reason for deviating from a guideline, the intermediary stores that reason in the Website database to be presented to the patient later in the process. When the patient accesses the Website (which is described below), one of the questions he/she is asked to answer is to rate or express an opinion about the doctor's reason for deviating from a guideline. As a result, the health plan is served (wins) because the doctor knows his/her reason for deviation (or for that matter, declaration of guideline adherence) will be rated by the patient, which may cause the patient's opinion of the doctor's care to be reinforced or diminished to the point the patient may refer the doctor to others or seek care elsewhere. Doctors are aware that their patients are gaining valuable information through the Program and doctors know that their patients will expect care that is aligned with evidence-based and/or recommended treatments. Doctors also become aware that they are being rated by their patients against evidenced-based and recommended care. Though this rating may or may not directly impact an individual doctor's compensation on a per-occurrence-of-care basis, most doctors do not want their aggregate rating to cause them to be ranked poorly against their peers or to suffer negative consequences because of a poor aggregate rating or a low ranking that may be published. This check and balance aspect of the current invention serves as an important incentive to encourage doctors to be adherent to guidelines or to provide appropriate reasons for deviation from a guideline.

Doctors are served (win) by the current invention because this check and balance feature alleviates the concerns medical practitioners (doctors) have about being forced to practice "cookbook medicine" and helps doctors better communicate and educate their patients. Patients are served (win) because the Program communicates their doctor's reason for deviation so patients can understand that a particular guideline does not necessary fit a specific medical condition. This feature also helps the developers of guidelines and medical researchers determine which guidelines are strongest and which ones need further research and development.

Another feature of the current invention provides for the efficient and effective dissemination of advancements in medicine to service providers (medical practitioners) and serves as a means (incentive system) to encourage doctors to adopt new and proven advancements in medicine. This feature accomplishes these objectives by highlighting new advancements in the decision-tree guidelines or medical content presented in the medical practitioner's Website. The Website can require the medical practitioner to read the highlighted guideline or content that contains research studies or literature that supports the advancement. The medical practitioner can also be required to answer a questionnaire or indicate an acknowledgement or take a test about the medical advancement in order for the medical practitioner to receive compensation and/or to earn the higher rates of reimbursement offered through the program. The successful completion of the questionnaire or test may earn the medical practitioner credits toward required continuing medical education (CME). The current invention may also forward (electronically or otherwise) the results of the questionnaire to the medical practitioner's licensure board. Since the doctor is already asked to declare adherence to the guideline or provide a reason for deviation from the guideline, adoption of medical advancements can be accelerated.

Though the service provider and patient psychological incentives are interactive in that both parties are aware that they will be asked to judge each other's declaration of adherence (or non-adherence) against their actual performance, the current invention ideally (but not necessarily) separates the financial reward provided to the medical practitioner from the reward provided to the patient. Thus, the medical practitioner may be paid for his/her time and effort independent (or dependent) of how the patients respond to their Ix or adherence to a performance standard. Patients' performance-based reward may be independent (or dependent) of the medical practitioners' participation, prescribing information therapy or adherence to other performance standards. However, the patients' financial rewards are generally dependent upon the patients' adherence to self-managing their health. In other words, a smoker most likely will not be rewarded for answering all Website questions correctly except for a statement of smoking cessation or a commitment to stop smoking. The rewards strategies have been purposely configured to create a natural and beneficial check and balance between doctors and the patients. This set of strategic checks and balances solves the issues of compliance monitoring and appropriate provider deviation from a guideline that other incentive-based models cannot resolve.

The current invention provides a method for delivering healthcare services designed to lower healthcare costs and improve patient clinical outcomes by elevating the standard of care and encouraging patients to lead healthier lives through a web-based, provider-patient interactive incentive (reward) system. An application of the method comprises the steps of receiving a claim for compensation for medical services from a medical practitioner for medical treatment of a patient covered by the invention's program. The claim 1ncludes at least one applicable diagnosis code corresponding to at least one applicable medical treatment (such as an office visit) received by said patient. If at least one diagnosis code in the submitted claim corresponds to a medical diagnosis found in a data base of applicable medical diagnoses, then a notice is sent by the independent intermediary, also known as an Informediary, to the medical practitioner, directing the medical practitioner to voluntarily access a Website operated by an Informediary. The Website presents the medical practitioner with EBM treatment guidelines or other pertinent medical content relating to the patient's medical diagnosis. In addition to the common medical treatment, the medical practitioner prescribes Ix for said patient that provides the patient with instructions concerning managing the medical condition and living a healthy lifestyle. The medical practitioner may be given the opportunity to rate the patient's compliance with the prescribed information therapy, recommended treatments, and instructions relating to a healthy lifestyle.

In another embodiment, the current invention provides a method for delivering healthcare services through a web-based, interactive provider-patient incentive (reward) system. One method of the current invention comprises the steps of the Informediary receiving a claim for compensation for services rendered from a medical practitioner for medical treatment of a patient. The claim presented by the medical practitioner includes at least one applicable diagnosis code corresponding to at least one applicable medical treatment rendered to said patient. Upon receipt the claim 1s examined to determine if at least one diagnosis code corresponds to an applicable medical diagnosis found in a data base of applicable medical diagnoses. If a corresponding applicable medical diagnosis is present, then a notice is sent by the Informediary to the medical practitioner. The notice sent to the medical practitioner includes the instructions necessary for accessing a Website. Once the medical practitioner gains access to the Website, the medical practitioner will have access to EBM treatment guidelines relating to the patient's medical diagnosis. Thereafter, the medical practitioner considers adherence to an EBM treatment guideline or supplies an appropriate reason for deviation from the guideline and then prescribes information therapy for the patient through the Website application. The prescribed information therapy includes instruction for the patient to self-manage his/her medical condition and guidelines for healthy behavior. Additionally, the medical practitioner rates patient compliance with the prescribed Ix and recommended health maintenance. Following prescription of Ix, the Informediary automatically generates a notice to be provided to the patient directing the patient to access the Website. Once the patient accesses the Website, the Website provides the patient with the means to access medical information relating to his/her medical diagnosis. The method further provides for the monitoring of the patient's access of the medical information. The Website further provides a knowledge exam design to measure patient comprehension of the medical diagnosis, how his/her doctor (medical practitioner) should be treating the diagnosis, and how the patient can self-manage his/her condition. Provided that the patient takes the exam, the Website will automatically score the knowledge exam and it will provide the patient with the option of (or require) forwarding the knowledge exam results to patient's health plan. The patient is also asked to indicate their personal adherence to recommended care and self-management, to report their health status, and to rate their medical practitioner's performance against the recommended care. Finally, the patient is provided with the option of authorizing the compliance rating assigned by his/her medical practitioner to the patient's health plan and/or employer for the purpose of determining a financial or other type of rewards.

In a further embodiment of the current invention, the patient is provided with the option of rating (or is required to rate) the medical practitioner's compliance with EBM treatment guidelines or other accepted care corresponding to the patient's diagnosis. In this embodiment of the invention, the patient is advised by the patient portion of the Website of a deviation from the EBM or other accepted care by his/her medical practitioner and provided with the medical practitioner's reason for the deviation. Following review of the prescribed Ix material, the patient is asked to consider the medical practitioner's care and judgment against medical science in order to rate the medical practitioner's performance. This rating ideally does not, though it may, directly affect that medical practitioner's reward or compensation on a case-by-case basis. However, it does begin to build an overall clinical performance rating for that medical practitioner. This can be used to help individual medical practitioners measure their performance against their peers. Poor ratings can be used in peer review. This embodiment of the invention allows and encourages medical practitioners the freedom to use their clinical judgment to deviate from a guideline while receiving the maximum financial reward, provided the medical practitioner selects or supplies a reason for the deviation. Preferably, the ratings provided by the medical practitioner and the patient would be obscured from each other to help protect the doctor-patient relationship with each party having the option of releasing their rating.

Still further, the current invention provides a method for delivering healthcare services through a web-based, interactive provider-patient incentive (reward) system. The system of the current invention comprises a Website operated by an Informediary and having a medical practitioner portion and a patient portion. The medical practitioner's portion is programmed to be accessed directly by the medical practitioner during the patient encounter or to receive a claim submitted by the medical practitioner after the patient encounter containing standard codes for the patient's diagnosis(es) and medical services rendered by the medical practitioner. The Website compares the medical diagnosis(es) supplied by the medical practitioner during the patient encounter or from a coded claim to a database of medical diagnoses. If the diagnosis(es) supplied during the patient encounter or submitted via a coded claim matches a medical diagnosis and/or medical service in the Website's database, then said Informediary sends a notice to said medical practitioner directing the medical practitioner to access said Website. The medical practitioner portion of the Website includes a database of EBM guidelines, patient names, dates of services provided and medical diagnoses accessible by the medical practitioner. The Website provides the medical practitioner with the ability to indicate their compliance with or reason for deviation from EBM guidelines for the medical treatment provided. Additionally, the Website provides for input by the medical practitioner of a patient's compliance with prescribed treatment. Further, the Website tracks the medical practitioner's usage of the Website to prevent fraud and abuse. Finally, the medical practitioner portion of the Website automatically assembles the information supplied by the medical practitioner to assign one of two or more reimbursement levels for each applicable medical service. These reimbursement levels are based upon specific rules of compensation that are established between a health plan (which has "bolted-on" the Program/invention and is offering the Program of the current invention) or intermediary and the medical practitioner through a provider service contract. These rules are constructed to compensate the medical practitioner for participation and adherence according to the Program's principles and contractual terms and conditions. The patient portion of the Website includes a database containing at least the information therapy relevant to the patient's condition, including medical treatment provided/prescribed by the medical practitioner. The Website is accessible by the patient and the Website provides the patient with a knowledge exam designed to assess the patient's understanding of the information therapy including prescribed medical treatments. The patient portion of the Website monitors the patient's access of the Website and scores the knowledge exam. Additionally, the patient portion of the Website provides the patient with the ability to direct the Informediary to forward the score results of said knowledge exam to a third party (health plan) to determine and affect a financial or other type of reward. Typically, the third party will be the patient's employer, health plan, and/or insurance provider. Finally, the patient portion of the Website provides the patient the option of authorizing the release of his/her medical practitioner's assessment of patient compliance with prescribed treatment to a third party to determine and affect a financial or other type of reward.

In a preferred embodiment, the present invention comprises an interactive Internet-based incentive system that rewards healthcare service providers and patients for demonstrating levels of performance directed toward improving the providers' standard of care and the patients' health behaviors. Improved standards of care and health behaviors lead to improved clinical outcomes and lower overall medical costs through the integration of performance standards such as evidence-based medicine (EBM) treatment guidelines, information therapy (Ix®), pre-authorization certification of medical services, hospital care services, pharmacy benefit management including e-prescription and automated drug interactions, personal health records, medical literacy, and health self-management. The present invention utilizes Internet-based applications and sets of performance standards in order to improve the flow of information to and between healthcare service providers. The service provider and patient are encouraged to participate through an interactive system of "checks and balances" between the service provider, the patients, and an independent intermediary. The check and balances system shapes the behavior of the service provider and the patient to promote a higher standard of care by the service provider, improve medical literacy, and encourage better health habits, all of which lead to improved clinical outcomes and lower healthcare costs.

®Ix is a register trademark of the Center for Information Therapy, Inc.

The "checks and balances" method and system directs healthcare purchasers and payers to offer performance-based incentives to healthcare service providers and patients when they individually access the invention's Internet-based applications to declare adherence to a standard of performance, and agree to have the other party confirm their declaration. The performance-based incentives may comprise financial as well as other types of rewards.

The present invention increases overall health, promotes a higher standard of care while allowing service providers the freedom to exercise clinical judgment, achieving provider and patient compliance though psychological incentives, preventing fraud and abuse, and accelerating the adoption of medical advancements.

The current invention provides methods for improving the standard of care and encouraging healthiness that lead to the lowering overall healthcare costs. The improved healthcare delivery methods achieve the desired results by focusing on those parties having the greatest control over healthcare costs, i.e. the medical practitioner and the patient. In particular the current invention integrates the roles of the patient and medical practitioner in determining the medical treatment.

The current invention's features and functionality affords many benefits to medical providers (physicians and hospitals), patients, and purchasers/payers (health plans). Some of these benefits include the following:

The Program is Designed to Be Fast and Easy for the Medical Practitioner to Use:
The Program's Website has been specifically designed to be fast and easy for the medical practitioner to use. Once a medical practitioner becomes familiar with the Program Website and the EBM guidelines, performance standards or medical content for the diagnoses they treat most frequently, the doctor can select his/her responses to the Website's questions in a matter of seconds. Alternatively, the guidelines and questions can be printed so the doctor can respond off-line. The doctor can also choose to delegate his/her responses to his/her nursing or clinical staff. In fact, the doctor can record his/her responses on a normal billing form to be entered into the Website by the doctor's discharge clerk as the patient checks-out.

The Program Helps Improve the Medical Practitioner's Productivity and Standard of Care:
Medical practitioners report that the Program helps them gain productivity by allowing them to prescribe information therapy (Ix) as opposed to taking the time to verbally explain medical information to their patients. Furthermore, the doctor is aware that the patient will be tested to confirm the patient's knowledge and understanding. This is clearly an improvement in the standard of care that is has been occurring in the deliver of healthcare prior to the development and adoption of the current invention.

The Program is Designed to Help Accelerate the Dissemination and Adoption of Medical Advancements:
Studies indicate that it takes, on average, a decade or more for the medical community to effectively adopt advancements in medicine. Another important application of the current invention is in accelerating the dissemination and adoption of medical advancements. The Program's Website can highlight sections of an EBM treatment guideline (decision-tree) or provide other types of information that advises medical providers on medical advancements as they occur. The Program's Website is designed to require the medical practitioner to read the studies and/or literature that support the medical advancement and to answer questions indicating the doctor's understanding of the advancement. The Website is also designed to require a doctor to complete this task at least once for each new medical advancement involving an associated diagnosis treated by the doctor before the Program will compensate the doctor. In other words, a doctor's compensation can be delayed or reduced until the doctor demonstrates an understanding and/or adherence to medical advancements (or provides an explanation for non-adherence). As added incentive, doctors can earn continuing medical education (CME) credits when they successfully complete the Website's medical advancement questionnaires. In fact, the Website can automatically report doctors' CME to their licensure board. Accelerating the adoption of medical advancements by using an Internet application, financial rewards and CME credits is clearly an improvement in the standard of care that is not occurring in the deliver of healthcare prior to the development of the current invention.

The Program Helps Improve and Doctor-Patient Communications:
Studies have shown that verbal communication between doctors and patients is poor, and that poor doctor-patient communication is a significant cause of misdiagnosis, less than optimal clinical outcomes, and higher costs.

The Program alleviates the problem of poor doctor-patient communication through information therapy (Ix) prescribed by doctors to their patients through the Program's Websites. Patients are then financially rewarded for accessing the Website (or telephone service) to read their information therapy and demonstrate their knowledge of their medical condition and understanding of how to self-manage their health to their doctor and the Website's independent intermediary. The Program is designed so that this process of doctor-patient communications occurs for each patient encounter. Thus, doctor and patient communications are further enhanced through reinforcement.

The Program Improves Patient Medical Literacy and Encourages Compliance:

The Program helps improve health by having patients demonstrate their understanding of the medical information prescribed to them by their doctor and by having patients declare their compliance through the patient's portion of the Program's Website. The Program enhances patient medical literacy and compliance in two important ways. First the Program allows health plans to offer patients an opportunity to earn financial rewards for reading medical information about their personal health and then successfully answering questionnaires on the Website to demonstrate their knowledge and compliance. Second, the patients are aware that their Website responses will be e-mailed or made available to their doctor. Since patients want to demonstrate knowledge of and compliance to health recommendations to their doctor, patients' awareness that their Website responses being made are available to their doctor helps promote patient medical literacy and compliance. In other words, patients will tend to be more compliant when they are aware that their doctor is being informed of their efforts to be compliant, or conversely, their lack of effort to be compliant. Clearly, the current invention's methods of combining financial rewards and with performance checks and balances between patients and their medical providers, which are administered and authenticated by an independent intermediary through a Internet service, create a unique incentive system that motivates the types of patient and medical provider behavior that improves the standard of care and the level of health, all of which leads to healthcare cost containment.

The Program Encourages Medical Practitioner Adherence to Evidence-Based Medicine and Recommended Care and Adoption of Medical Advancements:

An important study determined that doctors practice recommended care only about 55% of the time. This results in inferior clinical outcomes, harm to patient, and higher costs. The Program encourages medical practitioners to provide evidence-based and recommended treatments more frequently, adopt medical advancements more quickly, and incorporate other performance standards for a number of reasons to include the following:

The most obvious reason for physician participation and adherence to performance standards is because the Program compensates doctors to do so. Moreover, the current invention's economic basis supports not just compensating physicians but to compensate physicians well. Most pay-for-performance programs offer 1% to 5% additional compensation to physicians. The current invention offers 10% to 20% additional compensation and has still demonstrated a significant return on investment (ROI) to the health plan (purchaser/payer).

Another distinguishing characteristic of the current invention's compensation of both the medical provider and the patient is the timing and frequency of the compensation. Unlike other pay-for-performance programs which pay doctors at the end of an accounting period (annually, quarterly, monthly), the Program compensate doctors (and patient) more immediately on a per-occurrence-of-care basis. The immediacy of the Program's rewards is more "Pavlovian", which helps affect and reinforce positive performance.

Doctors are often frustrated with the lack of patient compliance with recommended care and unhealthy patient behaviors. They consider treating a non-compliant patient as merely enabling and perhaps encouraging poor health habits. Doctors realize that the current invention can be an effective tool to help them communicate better with their patients, confirm their patients' understanding, and serve as a means to encourage their patients to more compliant with recommended care and healthier behaviors.

Doctors are constantly concerned about medical malpractice. As a result, they are encouraged to practice defensive medicine, which involves ordering tests and providing other services that reduce the risk of malpractice liability but are not considered evidence-based treatments. Studies indicate that defensive medicine drives-up the cost of healthcare by 5% to 9%. The Program is designed to help reduce medical malpractice risk and the amount of defensive medicine. Since the doctor is documenting adherence (or reasons for non-adherence) to evidence-based medicine treatments on the Website, and the doctor is prescribing information therapy (Ix) to the patient on a per-occurrence-of-care basis, a higher standard of care is provided and a degree of medical malpractice risk management is achieved. Thus the Program helps prevent malpractice suits and adverse judgments, and could reduce medical malpractice insurance premiums for participating medical providers.

Doctors gain productivity each time they prescribe information therapy (Ix) through the Program. In effect, doctors save time spent on the tedious, time-consuming, and more often than not, ineffective verbal explanations and instructions to their patients. Time saved in each patient encounter can be used to treat more patients, which translates into an increase in doctor productivity and income generation. In addition, the doctor's office staff should expect to save time answering fewer patient telephone calls because patients become more medically literate after reading the medical content and answer questions on the Website.

Doctors want to provide the best possible care to their patients but may not be aware of which treatments are currently recommended. The Program's Website provides this information in a clear and concise manner. Doctors like the convenience of being able to access evidence-based medicine through the Program's Website. In general, the Program's Website medical content vendors offer a drill-down feature that permits doctors to exam the research studies and literature that support the decision-trees and recommended guidelines. This helps doctors provide a higher standard of care, which in turn helps improve clinical outcomes and lower costs.

Doctors want to communicate with their patients better and insure patients understand their medical condition and recommended treatments. Doctors want their patients to be compliant with the recommended care and become healthier. The Program's information therapy (Ix) feature allows doctors to accomplish these objectives, to include confirming of the patient's knowledge of and compliance with recommended care. This is unlike any other method and helps doctors provide a higher standard of care, which in turn helps improve clinical outcomes and lower costs.

The Program assigns the same rate of compensation whether the doctor declares adherence to an EBM treatment guideline or declare non-adherence to a guideline provided the doctor indicates the reason for his/her decision to deviate from a guideline and agrees to allow his/her patients to express their opinions about the doctor's reason for non-adherence (deviation). In this way, the Program alleviates doctors concerns about being forced to practice "cookbook medicine" like other pay-for-performance programs do. This helps doctors provide a higher standard of care, which in turn helps improve clinical outcomes and lower costs.

The Program helps doctors manage the care to their patients as opposed to having patients direct care through Internet searches and/or medicine advertising on television and other medium.

The Program provides a means for doctors to compete on the basis of objective, demonstrate-able quality against acceptable criteria as judged by their own patients, who must be qualified before they renders judgment. This is in contract to other medical provider ratings against complicated criteria as judged by health plans based on insufficient or inadequate information such as insurance claims data.

The Program Electronically Interfaces with Health Plans to Automate the Entire Process:

The Program is not an insurance company nor does it fund the financial rewards to the medical practitioner or the patient. The funding of these rewards is the responsibility of health plans who are customers of the Program, to include health insurance companies, governments, provider networks (PPOs), managed care organizations, and large self-insured employers. The Program has developed Website software applications and electronic interfaces with health plans to make the processing of opportunities, notifications, and participant compensation fully automated.

Preferably, the system of the current invention will provide suitable incentives to both the patient and the medical provider to bring about a change in behaviors resulting in an improved standard of care and an improved level of healthiness that leads to better clinical outcomes for the patient and lower overall costs for the healthcare system. Additionally, the improved method for delivering healthcare aligns the interests of all the key stakeholders in the healthcare industry. These key stakeholders are generally identified as medical providers (principally physicians and secondarily hospitals), patients (healthcare consumers), and healthcare purchasers/payers (self-insured employers; health insurance companies; and the governmental health programs such as Medicare, Medicaid, Veterans Administration, and Indian Health Service). For the purposes of this discussion, the current invention focuses on services delivered by a medical practitioner such as a physician; however, the methods of the current invention apply equally well to all medical service providers such as hospitals and other caregivers and healthcare providers. The healthcare delivery system provided herein will improve the standard of care, encourage healthiness, and lower costs.

The current invention provides these benefits by financially rewarding medical practitioners and patients through a "incentive-based" program. Since the current invention "triangulates the interests" of the key stakeholders in a "win-win-win" proposition, it may be better described as an "alignment of interest" of "AOI" arrangement. In the method of the current invention, patients and medical practitioners (medical providers) receive financial rewards when they voluntarily follow evidence-based medicine (EBM) guidelines and appropriately respond to questions relating to EBM and other performance standards, and when medical practitioners prescribed treatments including instructions relating to living a healthy lifestyle and managing the medical condition. Through use of "information therapy (Ix®)," the current invention empowers the patient, allowing the patient to take an active role in managing their own healthcare, thereby improving their overall quality of life. The combination of EBM, Ix, and other performance standards will improve the standard of care, foster healthiness, and lower overall healthcare costs.

® Ix is a registered trademark of Center for Information Therapy, Inc.

To encourage medical practitioner participation in the method of the current invention, medical practitioners will be financially rewarded (compensated) for each patient encounter when the medical practitioner accomplishes the following tasks for each treated diagnosis: 1) if available, consider EBM and other recommended treatment guidelines (and other performance standards) and indicate adherence to the guideline or deviation from the guideline for an appropriate reason that can or will be communicated to his/her patient through the Program Website, 2) prescribe information therapy to their patient (not optional for a financial reward), 3) rate the patient compliance to recommended care for each diagnosis, agree to have the patient rate the medical practitioner's declaration of adherence (or non-adherence), and 5) respond appropriately to patient responses on the Website to include warnings/alerts of patient medical issues.

Medical practitioners have the freedom to indicate their adherence to an EBM guideline or recommended treatment or to indicate their deviation from the guideline or recommended treatment for an appropriate reason supplied by the method or by the medical practitioner. The option to deviate from a guideline is offered to medical practitioners because their patients are subsequently asked to rate their medical practitioner's performance against the EBM or recommended treatment guideline during the patient's information therapy session. The patient's rating may be used to affect the medical practitioner's compensation directly or may be used to rate the medical practitioner against his/her peers or against other standards in an effort to improve performance or remove the medical practitioner from a health plan for gross aberrancy after due process. Thus, the method of the current invention provides medical practitioners with the freedom to adhere to or deviate from a guideline based on their sound clinical judgment while still being rewarded financially. In exchange for the right to practice medicine without rigid guidelines (directives), the medical practitioner allows the patient to review the prescribed treatment in view of the recommended or EBM treatment guidelines and other performance standards, and rate the medical practitioner's declarations of adherence or reason for non-adherence and performance against desired standards.

As an encouragement to respond to Ix prescriptions and to live a healthy lifestyle, the methods of the current invention enhances the financial outcome for participating patients when patients complete the following tasks 1) read the information presented to them on the methods webpages (Website) about their health condition, recommended (EBM) care and other pertinent performance standards; 2) answer questions presented on the Website to demonstrate their understanding of this information; 3) indicate their compliance to the recommended (EBM) and appropriate care or other beneficial performance standards; 4) report (or have health monitoring devices report) their health status such as weight, blood pressure, blood sugar, and resting heart rate; 5) authorize access to pharmacy records to verify that prescriptions have been filled or request verification that they have successfully participated in a health assessment or screening program, and/or authorize access to lab and other test results, and/or request verification that they have seen or scheduled to see a medical specialist or have successfully completed or scheduled to complete other recommended therapies, and/or authorize or affect the population of a personal health record with pertinent information and request his/her medical providers to use the personal health record in his/her treatment to achieve coordination of care and to prevent duplication of care, and/or participate in a pre-authorization certification of expensive tests and services (such as surgeries and hospitalizations) through the Website to prevent unnecessary procedures and insure better clinical outcomes, and/or demonstrate his/her healthy behavior by any other means; and 6) after acknowledging their medical practitioner's recorded responses to the Website question(s) about adherence to or reason for deviation from a recommended treatment or performance standard (and taking into consideration the information they have just read on the method's Website), rate their medical practitioner's adherence to the performance standard, and/or 7) as an option, elect to have (authorize that) their medical practitioner's rating of the patient's compliance to recommended and appropriate care (or other performance standards) be included the calculation to determine their financial reward or health status. (This election by the patient farther reinforces the Program's strategic checks and balances. Patients are aware that this election will cause the Program to compare their personal health compliance responses against their medical practitioner's rating of their health compliance. If the compliance indicators between the patient and the medical practitioner match, then the Program would indicate that the patient is be eligible for an additional financial reward from their health plan or purchaser/payer.)

The healthcare delivery methods of the current invention will be described with reference to FIGS. 1, 2 and 3. To aid in identification of the various steps of the current invention, identifying numbers are provided for selected portions of the process. Electronic communications, such as but not limited to the Internet and e-mail, provide the most efficient means for practicing the methods of the current invention. However, the methods of the current invention may be readily adapted to a telephone service, traditional mail, faxes and other hard copy communications or a blend of electronic communication and traditional communications.

Figure 2:
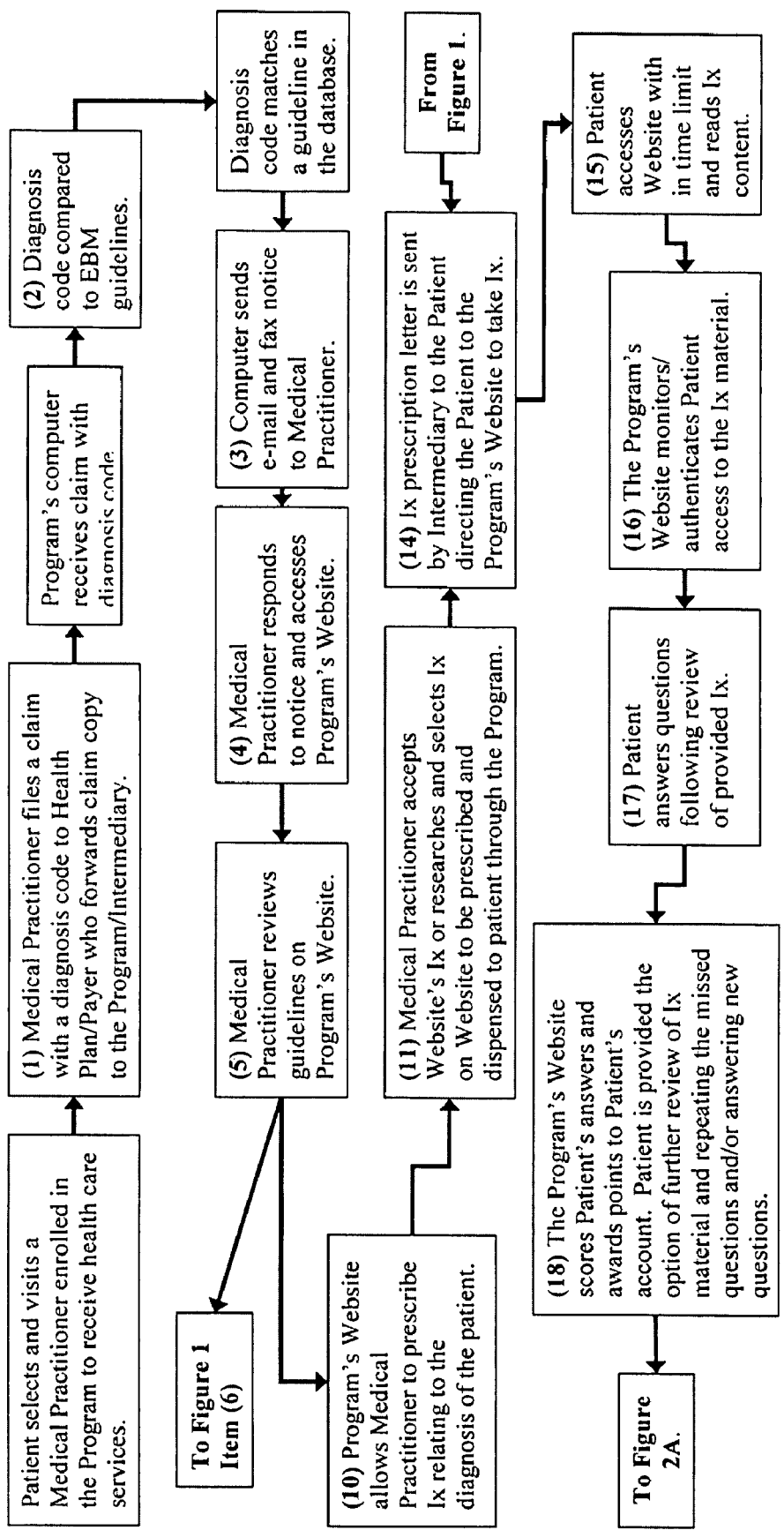
FIG. 2 is a flow chart representing the patient's portion of one embodiment of the Program.
Figure 2A:
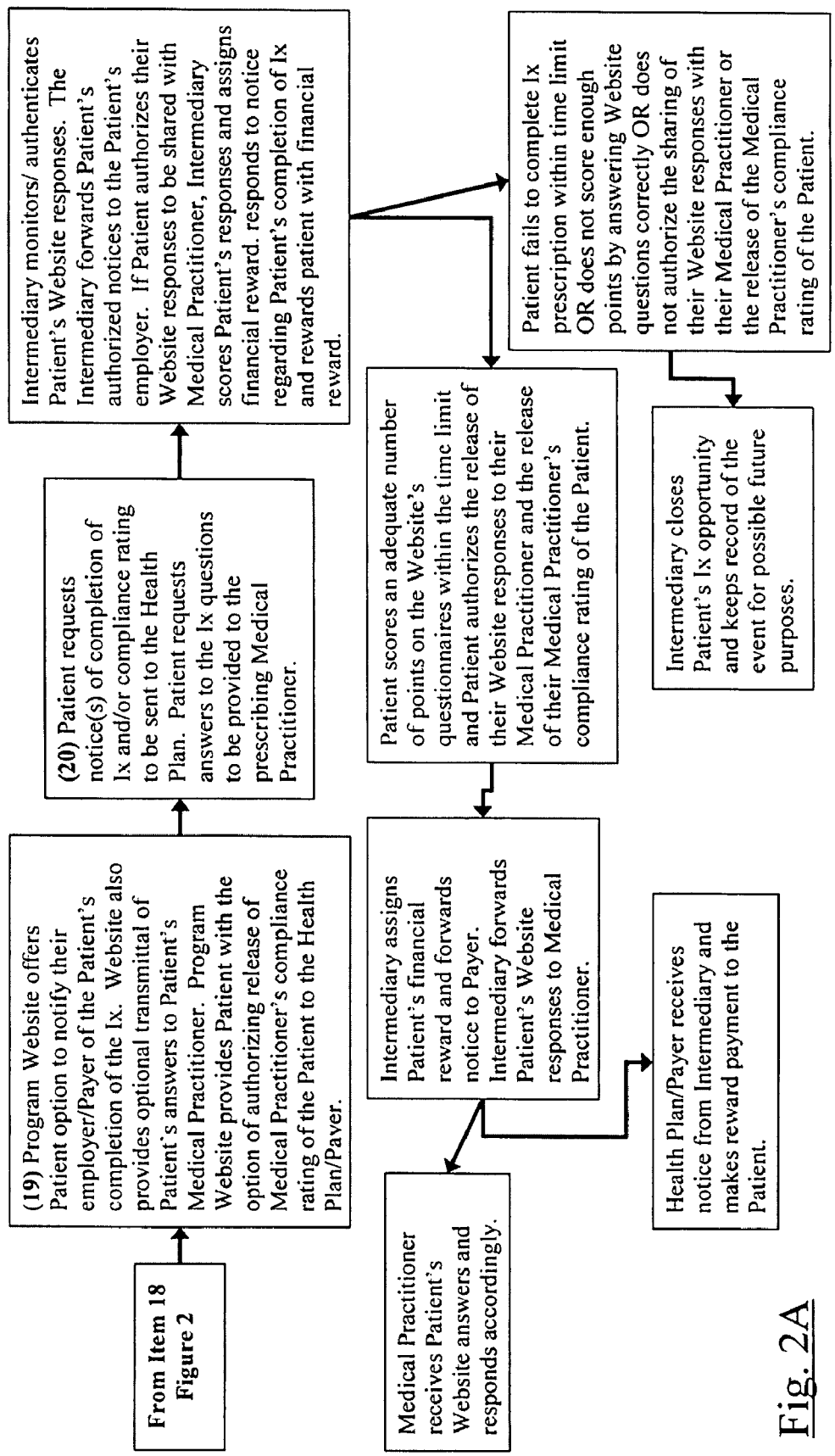

FIGS. 1 and 2 provide flow charts of the method for providing healthcare. FIG. 3 provides an illustrated description of the preferred embodiment of the current invention. FIG. 1 outlines an embodiment of the current invention as it relates to the medical practitioner's portion of EBM and Ix Therapy.

FIG. 2 outlines the patient's portion of an embodiment of the current invention. While shown in step wise format, those skilled in the art will recognize that various portions of the process can be moved earlier and later in the charts. The methods of the current invention are designed to provide flexibility and adaptability depending on the desires of the local health plan. The format of the current invention may be adapted by any form of health plan. Fee-for-service PPO's and governmental programs are particularly suited for performing the methods of the current invention. As used herein, the term "health plan" refers to the organization managing the healthcare delivery system and may include any payer type system including a self-insured employer, health insurance companies, managed care plans, and governmental programs such as Medicare, Medicaid, Veterans Administration, military, state and Federal employees, and Indian Health Service.

As shown in FIG. 1, the method of the current invention begins with educating the patient and the medical practitioner on why and how the methods of the current invention (referred to herein as "the Program") work. Medical practitioners are made aware of the Program by a variety of means to include organized meetings, targeted mailings and telephone contact, or with the aid of a local medical provider organization (medical provider organization licensee) contracted to sponsor the Program in the market. Medical practitioners are directed to the Program's Website to enroll online. Prior to receiving treatment, the patient identifies a medical practitioner that participates in the Program. Typically, the Program will be administered by an independent intermediary that operates the Website. The intermediary sells access agreements to purchasers/payers who offer health plans to employees or beneficiaries. The purchaser/payer "bolts-on" the Program to its health plan (that may be administered by an independent third party or TPA). It is the intermediary that will license medical provider organizations (such as a medical group practice, independent practice association or IPA, or a physician-hospital organization or PHO) to administer provider relations and promote the Program in its market. An example of these relationships is as follows; the independent intermediary sells a user license to the purchaser/payer. The purchaser/payer may comprise a self-insured employer and its employee health plan is administered by a health plan. The purchaser/payer directs the health plan to bolt-on the Program to the purchaser's employee health plan. Purchaser's employees and covered dependents, collectively, represent its health plan members. When a member seeks healthcare, they are described as patients. A patient seeking medical services presents themselves to the participating medical practitioner as a member of the purchaser/payer's health plan covered by the Program. Subsequently, the medical practitioner provides healthcare services to the patient.

Preferably, the medical practitioner accesses the Program's Website at the time of service (enrolls in the Program if he/she has not do so previously) and enters pertinent patient information and diagnosis(es) information preferably as a standardized diagnosis(es) code(s). (This preferred time of service method of practicing the Program is referred to as the point of service initiated or "POSI" real-time version as opposed to the claim 1nitiated or "CI" after-the-fact version that is described later.) The Website's software application compares the patient and diagnosis(es) information to the Program's data base. If the Program's software finds a patient information match in the Program's data base and there is available EBM or recommended treatment guidelines and Ix content related to the diagnosis(es) in the data base, then the Program displays the treatment guideline and/or Ix content to the medical practitioner on the Website. The Website is interactive. As such, if an EBM or recommended treatment guideline is available, the medical practitioner considers the guideline and indicates adherence to the guideline or provides a reason for deviation from the guideline on the Website. If Ix content is available, the provider selects or searches for the preferred Ix content and orders the Ix prescription to the patient on the Website. Optionally, the medical practitioner is asked to rate the patient's compliance to EBM or appropriate care for each presenting diagnosis. Optionally, the medical practitioner may be asked to consider or initiate other types of performances standards such a pre-authorization certification for certain heavy cost medical service, or a pharmacy benefits management service to include electronic prescriptions and lower cost therapeutic substitutions, or the updating of the patient's web-based personal health record, etc. The patient and diagnosis(es) information, the medical practitioner's response(s) to guideline adherence, the Ix prescription order, the medical practitioner's rating of the patient's compliance, and responses to other performance standards are stored in the Website's database for subsequent processing to determine the medical practitioner's rate of reimbursement.

The Ix prescription can be made available to the medical practitioner at the time of service so it can be printed and handed to the patient or it can be mailed or e-mailed to the patient. Alternating, the medical practitioner may choose to postpone reviewing guidelines and prescribing Ix until after an insurance claim for reimbursement of the medical services is filed. Therefore the process can be initiated at the time of service by the medical practitioner accessing the Program's Website or it can be initiated by filing an insurance claim for normal medical services reimbursement.

Following treatment of the patient, the medical practitioner files an insurance claim for medical services reimbursement with the Health Plan administrator. Preferably, the medical practitioner files the claim electronically (1). The medical claim contains information commonly found on current claim forms such as % the patient's name, the medical practitioner's name, a primary medical diagnosis, secondary diagnosis(es) and the service provided by the medical practitioner. Preferably, the medical diagnosis and the medical services are identified by a usual and customary diagnosis medical services codes, and the diagnosis(es) is appropriately linked to the corresponding medical service(s). The Health Plan simultaneously processes the claim as usual, but also forwards a copy of the claim to the intermediary.

Upon receipt of the claim, patient and diagnoses information are compared by the intermediary to any matching information in the Program's database from the time of service. Matches then determine if the claim lists medical services eligible for a variable rate of reimbursement (referred to as "applicable medical service(s)") contained in the Program's database (2). If the claim contains applicable medical services, then the medical practitioner's stored responses to the Website queries concerning guideline adherence, Ix prescription, patient compliance for the diagnosis(es), and performance of other standards linked to the applicable medical services are taken into consideration in determining the medical practitioner's rate of reimbursement (compensation) as described herein.

Medical practitioners must submit an insurance claim for medical service reimbursement within a time limit or they will not be eligible for the higher rates of reimbursement or any compensation associated with the Program for that patient encounter. (Missing the time limit for filing a claim would not necessarily affect future opportunities to practice the Program.) If information supplied by the medical practitioner at time of service is not matched to a claim within a certain period of time, then the Program may send a warning to the medical practitioner that the claim filing time limit is running out.

Alternatively, if the medical practitioner did not access the Website or respond to the Website queries at the time of service, then the Program's (intermediary's) computer will not identify matching patient and diagnosis information. If this is the case, then the computer compares the claim 1nformation to the Program's database for applicable diagnoses. If the claim contains an applicable diagnosis, then the computer determines if the diagnosis is linked to an applicable medical service. If this is the case, then the medical practitioner receives a notification informing the medical practitioner that there are EBM guidelines and Ix content available for review (3). (This after-the-fact method defines the claim 1nitiated or CI version of the Program.)

In the preferred embodiment, the intermediary's computer capable of comparing the diagnosis and medical service(s) codes to the Program's database receives the claim. If the encoded diagnosis and corresponding medical service(s) matches the code for medical diagnosis and applicable medical services within the Program's database, then the computer automatically transmits an email, fax or other electronic correspondence to the medical practitioner, or the computer system prepares a regular letter for mailing to the medical practitioner.

The notification sent to the medical practitioner advises the medical practitioner to access the medical practitioner's portion of the Program's Website containing EBM guidelines or other healthcare quality improvement and cost control methods (collectively referred to as performance standards). The Program Website is preferably a secure website requiring input of the medical practitioner's password to gain access to the data contained therein. Alternatively, these codes may be transmitted by a separate email or otherwise provided to the medical practitioner. The method for gaining access to the Website is not critical to the current invention.

For the purposes of this disclosure the term website refers to the Program's Websites. The Program's Websites may or may not be located on a central server at the intermediary. Further, the patient and practitioner portions of the Program's Websites are not necessarily contained on the same computer system, but may be maintained by purchasers/payers' computers or multiple independent intermediaries. As used herein, the medical practitioner portion of the Program's Website will preferably be utilized by all parties authorized to access the medical practitioner's portion of the Website including but not limited to nurses, nurse practitioners, physician assistants and other care providers.

Upon entry of the appropriate codes or passwords at the Website (4), the Website identifies the names of patients, the dates and types of services provided, the medical diagnoses and related medical services for the accessing practitioner or his/her authorized assistant. The Website also provides the available EBM guidelines or other healthcare quality improvement and cost control methods (performance standards) corresponding to each diagnosis. Preferably, the medical practitioner reviews and confirms the appropriateness of the information found on the Website (5).

The Program's Website is interactive. As such, it queries the medical practitioner concerning adherence to EBM guidelines or other healthcare quality improvement and cost control methods performance standards) for the diagnoses (6), the prescription of Ix to the patient, and patient compliance with the prescribed treatment and guidelines on living a health lifestyle and methods for controlling/managing the patient's medical condition (12). The medical practitioner's response to the queries will determine the reimbursement rate used to compensate the medical practitioner for services rendered on each claim associated with a Program "opportunity." If the medical practitioner responds to the query concerning patient compliance, confirms the prescription of Ix to the patient, and confirms treatment within the scope of the EBM guidelines or other healthcare quality improvement and cost control methods (performance standards) or provides appropriate reason(s) for deviation from guidelines and methods (7), then the Website will automatically direct compensation to be made according to a higher payment (practitioner reimbursement) rate scale (13). Preferably, the highest rate of medical practitioner compensation (payment) is selected when the medical practitioner practices the method on a real-time basis using the POSI version of the Program. (Timeliness can be important in delivering information therapy and other services initiated through the Program to the patient. Therefore, the highest rate of medical practitioner compensation is typically assigned when the POSI version of the Program is practiced.) Alternatively, the highest rate of compensation can be assigned in instances where the medical practitioner has indicated adherence to or deviation from (with appropriate reason) a recommended treatment guideline, prescribed Ix for the patient (10, 11) and has rated patient compliance (12). (It should be noted that additional medical practitioner compensation can be earned through the Program as other performance standards are added to achieve the intended objectives.) Typically, a secondary level or lower rate of compensation (payment) is assigned (selected) when the medical practitioner practices the after-the-fact CI version of the Program. Alternatively, the secondary level of compensation can be assigned (selected) when the medical practitioner has prescribed Ix for the patient and has rated patient compliance, but no treatment guideline is available.

As noted above, the Website also queries the medical practitioner concerning the patient's compliance with EBM guidelines, Ix and any lifestyle activities necessary to improve the patient's wellness. Preferably, the Website will provide the medical practitioner with the opportunity to rate patient compliance (12) with the recommended treatment and behaviors using the following terms: Compliant Partially Compliant, Non-compliant and Non-applicable. Alternatively, the patient compliance rating terms may be: Compliant and No Response. No Response may mean partially compliant, non-compliant, or non-applicable. To receive the highest compensation level (13) for the services provided, the medical practitioner may need to respond to the request for a patient compliance rating. The ratings provided by the medical practitioner will be stored by the Program awaiting a response by the patient to the prescribed Ix. However, the patient will not have the ability to see the medical practitioner's rating unless the medical practitioner has selected the option to permit patient viewing of the rating.

Typically, the medical practitioner must access the interactive Website within 48 to 72 hours of receipt of the after-the-fact, CI notification in order to qualify for the higher payment rate scale. In the preferred embodiment, the medical practitioner is required to respond to the notice within 48 to 96 hours or two to four business days. If the medical practitioner does not respond within the indicated period of time (8), then the Website will direct compensation to be made according to a lower (or lowest) rate scale or to not make any compensation in association with practicing the Program at all.

As previously indicated, the Program's Website is interactive. To provide the maximum flexibility and greatest possibility of improved clinical outcome for the patient, the method of the current invention does not rigidly limit the medical practitioner only to the EBM guidelines in order to receive the highest degree of compensation. Rather, the Program's Website provides the medical practitioner with the option of indicating the treatment falls outside of the guidelines while explaining the reason for prescribing treatment outside of the guidelines. Provided that the medical practitioner completes the section describing an appropriate reason for non-adherent treatment (8a), the Program's Website will still select the highest compensation level for the medical practitioner (13). Thus, the present invention avoids the practice of "cookbook medicine" by encouraging the medical practitioner to use appropriate judgment and medical skill when deciding to follow the EBM guidelines or choosing to deviate from the guidelines. As previously indicated, in the preferred method the medical practitioner must prescribe Ix for the patient and (alternatively) rate patient compliance with directions/guidelines on living a healthy lifestyle and other methods for controlling/managing the medical condition (12) before becoming eligible to receive payment at the highest or second highest (intermediate) compensation rates.

While the medical practitioner is not required to indicate compliance with the EBM guidelines, failure to respond within 48 to 96 hours or indicating non-adherence without providing an appropriate reason for treatment outside of the EBM guidelines will have a negative financial impact on the medical practitioner. Specifically, these actions will trigger the computer system to select the lowest possible payment scale for the medical practitioner's services (8c) or terminate that opportunity for the medical practitioner to earn additional compensation. If the medical practitioner fails to prescribe Ix for the patient, then the Website will direct the selection of the lowest payment scale for compensation of the medical practitioner or not compensation the medical practitioner for that opportunity.

Thus, the method of the current system provides a financial incentive to the medical practitioner to follow the EBM guidelines or to provide an appropriate reason for deviating from these guidelines. Additionally, the method of the current invention provides a financial incentive to the medical practitioner to prescribe Ix to the patient and to rate patient compliance with the prescribed treatment/lifestyle necessary to manage the medical condition (12). Furthermore, the method of the current invention provides a financial incentive to the medical practitioner to practice the Program on a real-time basis as opposed to after-the-fact. However, the method uses financial incentives to create other perhaps stronger incentives for the medical practitioner to practice the method. These incentives include the medical practitioner's desire to: 1) improve communications with his/her patients; 2) improve his/her patients' understand of their medical condition and how to self-manage their health; 3) provide a means to help patients be more compliant to recommended care and adopt and maintain better health habits; 4) increase his/her productivity; 5) gain a degree of medical malpractice risk management; 6) have access to the latest and best methods for treating diseases and injuries; 7) incorporate other beneficial performance standards; and last but not least 8) prevent his/her patients and others from thinking he/she practices inferior healthcare or, worse yet, learn that he/she is not truthful about what kind of medicine he/she practices. This final ($8^{th}$) incentive describes one of the checks and balances that are unique to the current invention. In effect, the medical practitioner is aware that his/her patient earns a financial reward for becoming qualified to rate the practitioner's adherence to and performance against high and beneficial standards. The medical practitioner is also aware that his/her patients' ratings will be aggregated and compared to his/her peers. This is a powerful incentive that encourages medical practitioners to participate in the Program and to practice medicine that is recommended by the medical profession or to provide appropriate reasons for non-adherence. In general, treatment according to the EBM guidelines and appropriate treatment outside of the guidelines coupled with patient compliance with treatment protocols and a healthy lifestyle will produce better clinical outcomes for the patient. Further, the prescription of Ix to the patient empowers the patient to be more compliant with their medical practitioner's treatment orders and instructions leading to improved clinical outcomes. Additionally, the patient's access to Ix provides the patient with the tools to control the medical condition thereby reducing doctor visits, the need for pharmacy and other therapies, and expensive hospitalizations. Thus, the current invention provides a method for improving clinical outcomes, promoting healthiness, and for reducing healthcare costs. Clearly, the current invention integrates the activities of the patient and medical practitioner by encouraging the incorporation of EBM, Ix and other beneficial performance standards with financial and other types of incentives.

In order to provide practitioner compliance and to prevent fraud and abuse, the Program's Website provides the means to monitor and audit the medical practitioner. In one aspect, the Website provides the means for tracking the medical practitioner's access to the Website. This tracking mechanism provides an indication of the medical practitioner's use of the EBM guidelines. For example, the Program's Website tracks the access time for each webpage reviewed, if the time of usage for each page does not meet a predetermined minimum, then the medical practitioner may be questioned concerning the legitimate usage of the EBM guidelines. However, the predetermined minimum time period for accessing a webpage is not a rigid requirement. Rather, the minimum access time period may vary from practitioner to practitioner and from diagnosis to diagnosis based on various parameters such as but not limited to the medical practitioner's area of expertise and experience and whether a particular webpage has been previously reviewed and/or printed by the medical practitioner. If a new medical treatment is established as recommended by the medical community and is new in a EBM treatment guideline, then the invention's Website application may prevent the medical practitioner from exiting that webpage or from receiving a higher rate of reimbursement or additional compensation until the medical practitioner "drills-down" into the application to learn about this new medical development, advancement, and/or treatment.

In another aspect, the Website provides the means for monitoring the frequency of treatments outside of the EBM guidelines (8 and 8b). Thus, the current invention provides health plans using the methods of the current invention with the ability to audit medical practitioners who may not be using the best treatments for their patients by using treatments outside of generally accepted procedures. As indicated above, the methods of the current invention are flexible and can be adjusted for individual practitioners on the basis of their practice area and experience and also adjusted to incorporate additional types of performance standards linked to specific incentives (as long as one or more incentive is interactive involving checks and balances between the medical practitioner and the patient) to achieve the objectives of better health and better and more affordable healthcare. The current inventions capability to adjust and expand performance standards and incentive to achieve specific objectives is referred to as "precision-guided incentives and performance standards."

Preferably, the medical practitioner accesses the Website from time to time to obtain the current EBM guidelines for diagnoses common to the medical practitioner's field. Thus, the Website provides an additional source of reference and education for the medical practitioner.

In instances where the medical practitioner's diagnosis does not correspond to a diagnosis contained in the EBM data base (9), then a notification to access the Program's Website will not be sent to the medical practitioner. Under these conditions, the Health Plan will direct the payer to compensate the medical practitioner at an intermediate rate. Alternatively, the Program may notify the medical practitioner that there is no medical content available for a particular diagnosis, so the medical practitioners earn compensation by supplying their own medical content (printed and handed or sent, or emailed from the Internet) their patients. (It should be noted that medical content exists through the Program for nearly 99% of diagnoses.) Preferably, the medical practitioner will continue to file claims for compensation via email or other electronic means even when a guideline or medical content does not exist for a specific diagnosis. As noted above, an electronically filed claim 1s "read" by a computer. When the computer does not find a diagnosis code corresponding to a medical diagnosis in the Program's database, the intermediary's computer will automatically direct compensation to be paid according to an intermediate rate scale, or the intermediary will notify the medical practitioner of the lack of medical content and offer him/her an opportunity to earn compensation by providing his/her own medical content to the patient.

The foregoing steps of the method of the current invention provide an incentive to the medical practitioner to comply with the treatments specified in the EBM guideline database and to rate patient compliance with prescribed treatment/lifestyle necessary to manage the medical condition. The treatments specified in the EBM database are the preferred treatments as determined by leading medical schools in the United States. In particular, the following schools conduct rigorous reviews of medical trials and literature to provide guidelines for treatments generally accepted by medical practitioners as the preferred or evidence-based treatments for the identified medical conditions. Schools currently developing preferred treatment guidelines include: Duke, Vanderbilt, Emory, and Oregon Health and Science University.

Providing an incentive to the medical practitioner addresses only one part of the total cost of healthcare. In order to further improve the patient's clinical outcome, promote healthiness, and enhance healthcare cost control, the patient must also play a role. Accordingly, the methods of the current invention provide an incentive to the patient to take a proactive approach to recovery from and prevention of medical conditions.

With reference now to FIG. 2, the method of the current invention provides the medical practitioner with the option of prescribing Ix for the patient (10). In the preferred embodiment, the method encourages the medical practitioner to prescribe Ix for the patient by rewarding the medical practitioner with a higher rate of compensation. Preferably, the medical practitioner will prescribe the Ix at the same time the medical practitioner is responding to the Website's inquiry regarding medical practitioner's compliance with EBM guidelines for the prescribed medical treatment. The prescribed Ix will normally be provided via an Internet website or a telephone service. For the remainder of this discussion, the source for the prescribed Ix will be referred to as the Program's Website; however, other sources of information are within the scope of the present invention.

If the medical practitioner prescribes Ix for the patient (11), then a notice in the form of an e-mail, fax, letter or other similar communication will be sent automatically to the patient by the Program or handed to the patient at the time of service by the medical practitioner (or the practitioner's staff). This patient notification (14) may contain the medical information or more preferably the notice will contain the information required by the patient to gain access to the Program's Website.

Upon receipt of the correspondence, the patient is expected to successfully accomplish the following tasks to earn a financial reward: 1) read the information presented to them on the patient portion of the Program Website about his/her health condition, recommended (EBM) care, other pertinent and beneficial performance standards; 2) answer questions presented on the Website to demonstrate their understanding of this information; 3) indicate their compliance to the recommended (EBM) and appropriate care or other beneficial performance standards; 4) report (or have health monitoring devices report) his/her health status such as weight blood pressure, blood sugar, and resting heart rate; 5) authorize to access pharmacy records to verify that prescriptions have been filled, and/or request verification that the patient has successfully participated in a health assessment and/or screening program, and/or authorize access to lab and other test results, and/or request verification that the patient has seen or is scheduled to see a medical specialist or has successfully completed or scheduled to complete other recommended therapies and/or authorize or affect the population of a personal health record with pertinent information and request his/her medical providers to use the personal health record in his/her treatment to achieve coordination of care and to prevent duplication of care, and/or participate in a pre-authorization certification of expensive tests and services (such as surgeries and hospitalizations) through the Website to prevent unnecessary procedures and insure better clinical outcomes, and/or demonstrate his/her healthy behavior by any other means; and/or 6) after acknowledging their medical practitioner's recorded responses to the Website question(s) about adherence to or reason for deviation from a recommended treatment or other performance standards (and taking into consideration the information he/she have just read on the method's Website), rate his/her medical practitioner's adherence to the performance standard, and/or 7) as an option, elect to have their medical practitioner's rating of his/her compliance to the prescribed treatment and Ix (or other performance standards) be included in the calculation of the patient's financial reward. (This election by the patient reinforces the Progam's strategic checks and balances that the patient is aware will cause the Program to compare the patient's personal health compliance responses against his/her medical practitioner's rating of his/her health compliance. If the compliance indicators between the patient and the medical practitioner match, then the Program would indicate that the patient is be eligible for an additional financial reward from his/her Health Plan.)

With reference to FIG. 2, the patient is expected to review the medical information made available by the Program's Website (15). The review of the prescribed Ix material is supplemented with a questionnaire to be completed by the patient (17). In the preferred embodiment, the Program's Website also provides the means to monitor the patient's access of the Website and completion of the questionnaire (16). This monitoring aspect provides the network with the means to audit patient compliance with the Ix and other treatment prescribed by his/her practitioner. Further, the monitoring system provides the ability to award "points" to the patient for reading the Ix, and for answering questionnaires which indicate the patient's knowledge and adherence to recommended treatments. As a means to insure compliance and prevent fraud and abuse the network can designate a minimum period of access time necessary prior to awarding a point for reviewing that section of the Ix. By requiring a minimum time period, the method of the current invention ensures that the patient performs more than a cursory review of the information provided.

Following completion of the questionnaires that tests the patient's knowledge and adherence to recommended and appropriate care, and rates his/her medical practitioner performance against recommended and appropriate care; the Website scores the patient's answers and awards points to the patient's account on the basis of the results (18). Following scoring, the patient has the option of further reviewing the Ix and repeating the questions or answering additional questions. Thus, the current invention provides the patient with the ability to gain further knowledge of his/her condition while enhancing the number of points awarded to his/her account. Clearly, the comprehensive nature and flexibility of the Program's Website provides the patient with the tools necessary to improve the clinical outcome of his/her treatment and to improve his/her overall general health. Optionally, Health Plan may elect to award patients with additional points and financial rewards for reviewing other medical information and accomplishing other performance standards intended to improve health and control cost, that are made available through the Program.

Upon completion of the Ix and indication of adherence and understanding of recommended and appropriate care, and the rating of his/her medical practitioner's performance; the patient is provided with a means for notifying the Health Plan of the receipt and review of the Ix material (19). Additionally, the patient will be provided with the option of sharing the medical practitioner's rating of patient compliance with the Health Plan. Typically, the patient will be provided with separate option boxes or other "clickable" devices on the Website to indicate the patient's desire to share the medical practitioner's compliance rating and to transmit a notice of completion of the Ix material to the Health Plan and/or employer. In the preferred embodiment the Program Website transmits the patient's actual responses to the questionnaire completed in step 18 to the medical practitioner. Though these choices are optional to the patient, if the patient elects not to share information, then the health plan (purchaser/payer) will most likely not provide the financial reward(s) to the patient.

In view of the incentives offered by the method of the current invention, the patient will likely request transmission of such notices to the health plan and/or employer (20). Upon receipt of such notices, the Health Plan has the option of providing a financial reward to the patient based on the patient's completion of the Ix material, rating of their practitioner, and the patient's compliance rating as provided by the medical practitioner. In keeping with the flexible nature of the current invention, the financial reward may be granted upon the completion of each prescribed Ix and practitioner rating portion. Alternatively, the party paying the reward may establish point thresholds for payouts. In the case of point thresholds, the patient's points are accumulated and upon reaching a predetermined level the financial reward can be paid to the patient.

As noted above, the method of the current invention preferably includes the medical practitioner's confirmation of the patient's application of the Ix therapy and patient compliance with the prescribed treatment/lifestyle necessary to manage the medical condition. In the preferred embodiment, point awards are conditioned upon the patient practicing the knowledge gained through Ix and making lifestyle changes prescribed by the medical practitioner. Accordingly, if the patient has been diagnosed with heart disease and has indicated full treatment adherence but has not taken preventive measures indicated by the Ix such as exercising and quitting smoking, then when the medical practitioner completes the patient rating portion of the medical practitioner's Website, the medical practitioner will either indicate Non-compliant or Partially Compliant or No Response. The network would then have the option of deducting points as well as adjusting the patient's co-pay and/or deductible and/or taking other more severe steps. The process of the patient sharing information with his/her medical practitioner and health plan and/or intermediary creates another check and balance that is designed to help improve healthiness and control costs. In effect, the patient is aware that he/she answers to questions on the Website (or over the telephone) about his/her compliance to beneficial performance standards will be available to his/her medical practitioner, health plan, and intermediary for review and authentication. The patient's desire to demonstrate to his/her knowledge and compliance to his/her medical practitioner is a strong motivator. The consequences of being untruthful in his/her responses on the Website are also a powerful incentive.

Finally, the current invention also preferably provides for patient inquiries of the medical practitioner through the Website, by e-mail or other similar means, during the Ix. Thus, the current invention integrates the patient's Ix with the medical practitioner's medical treatment and provides financial rewards to the patient based on completing the educational aspects of Ix as well as financial rewards for practicing a healthy lifestyle and adherence to treatment protocols as directed by the medical practitioner, and for rating their practitioner performance against recommended and appropriate care.

In accordance with the Health Insurance Portability and Accountability Act (HIPAA), the notice to the health plan and any notices to any other third parties will not divulge any protected patient health information unless arrangements have been made to meet HIPAA requirements.

In the method, the service provider and patient may be required to perform an action or physical act to declare adherence to a performance standard. An action or physical act may or may not be captured on the Website. In the case of an action or physical act, the service provider and patient would be expected to demonstrate adherence to a performance standard. Since the action or physical act may be captured by the Website, then the service provider and patient would be asked to acknowledge the action or physical act of each other. This implies that the action or physical act can be independently verified by the acknowledging party and authenticated by the intermediary. An example of a performance standard involving a verifiable action is the service provider electronically prescribing drug therapy to the patient through the Website. Since this action is captured by the Website, the method would ask the patient to acknowledge his/her service provider's adherence to the performance standard. Therefore, the terms "declare and confirm" and "declaration and confirmation" are synonymous to "demonstrate and acknowledge" and "demonstration and acknowledgment" when a verifiable action or physical act is involved.

The present invention is designed to allow the health plan (purchaser/payer) and the intermediary to select (or determine) a variety or varying amount of performance-based incentives depending upon the level or degree of adherence or performance by the service provider and the patient against a performance standard or multiple performance standards. An example of this feature involves establishing one amount of compensation for the service provider when he/she prescribes information therapy to the patient and an additional (or separate) amount of compensation when he/she uses a drug therapy management system to electronically prescribe pharmacy to the patient. In this case, the intermediary would authenticate the service provider's performance and determine the level of performance-based incentive to be paid to the service provider. Alternatively, the method may require the patient to confirm and acknowledge the service provider's performance in addition to the intermediary's authentication to determine the level of adherence (performance) and compensation.

Another embodiment of the present invention comprises pre-authorization certification programs that integrate the patient into the authorization process. This is referred to as "patient-integrated pre-authorization certification." In effect, patient-integrated pre-authorization certification involves the compensating the service provider for prescribing an informed consent through the Website to the patient when expensive or risky medical services (such as surgeries or hospitalization) are planned. The patient is financially rewarded for reading about his/her conditions, the planned treatment and treatment alternatives. The patient would then be required to demonstrate his/her knowledge by taking a test so he/she can be qualified to authorize the planned treatment or ask their physician about alternative treatments or seek a second opinion.

Another embodiment of the present invention comprises an enhancement to hospital care management systems by integrating patients into the hospital care process. This is referred to as "patient-integrated hospital care management." In effect, patients earn financial rewards for performing certain tasks associated with their hospitalizations. One such task is to designate a personal advocate such as a family member or friend. This method of the invention compensates hospitals and attending physicians for prescribing a hospital care plan and discharge instructions through the Website or during admission and at discharge to the patient and his/her advocate. After discharge, the patient and/or advocate would be queried through the Website to demonstrate their knowledge of the hospital care plan and discharge instructions. The Website then asks the patient and advocate to rate the hospital's and attending physician's performance against the hospital care plan. The patient would be asked to declare his/her compliance to hospital care plan and discharge instructions. As a means for the intermediary to authenticate performance, the hospital and attending physician could also be required to access the Website to enter the name of patient's advocate and to indicate the patient's adherence to the hospital care plan.

Clearly, the method of the current invention provides an incentive to the patient to take an active role in managing their medical condition. As a result, the clinical outcome of the patient's medical treatment will be enhanced. Thus, the methods of the current invention enhance the quality of medical care by encouraging the patient and medical practitioner through financial rewards and profound checks and balances to adhere to the scientifically proven best treatment guidelines or preferred methods and other performance standards, and by enabling the patient to manage the treatment of the medical condition to achieve a level of health. By enhancing the quality of medical care and increasing the patient's ability to manage their medical condition, the current invention encourages healthiness and reduces the overall costs of healthcare while providing an increase in compensation to the medical practitioner and a financial reward to the patient.

Collectively, the descriptions and illustrations presented herein and the terms such as "checks and balances", "declare and confirm", "demonstrate and acknowledge", "triangulation", "win-win-win", "precision-guided incentives and performance standards", and "alignment of interest" or "AOI" define the invention's unique "interactive" characteristics between medical providers and patients, and purchasers/payers. Hence, the invention can be accurately described as a "web-based interactive provider-patient incentive system."

Figure 3:
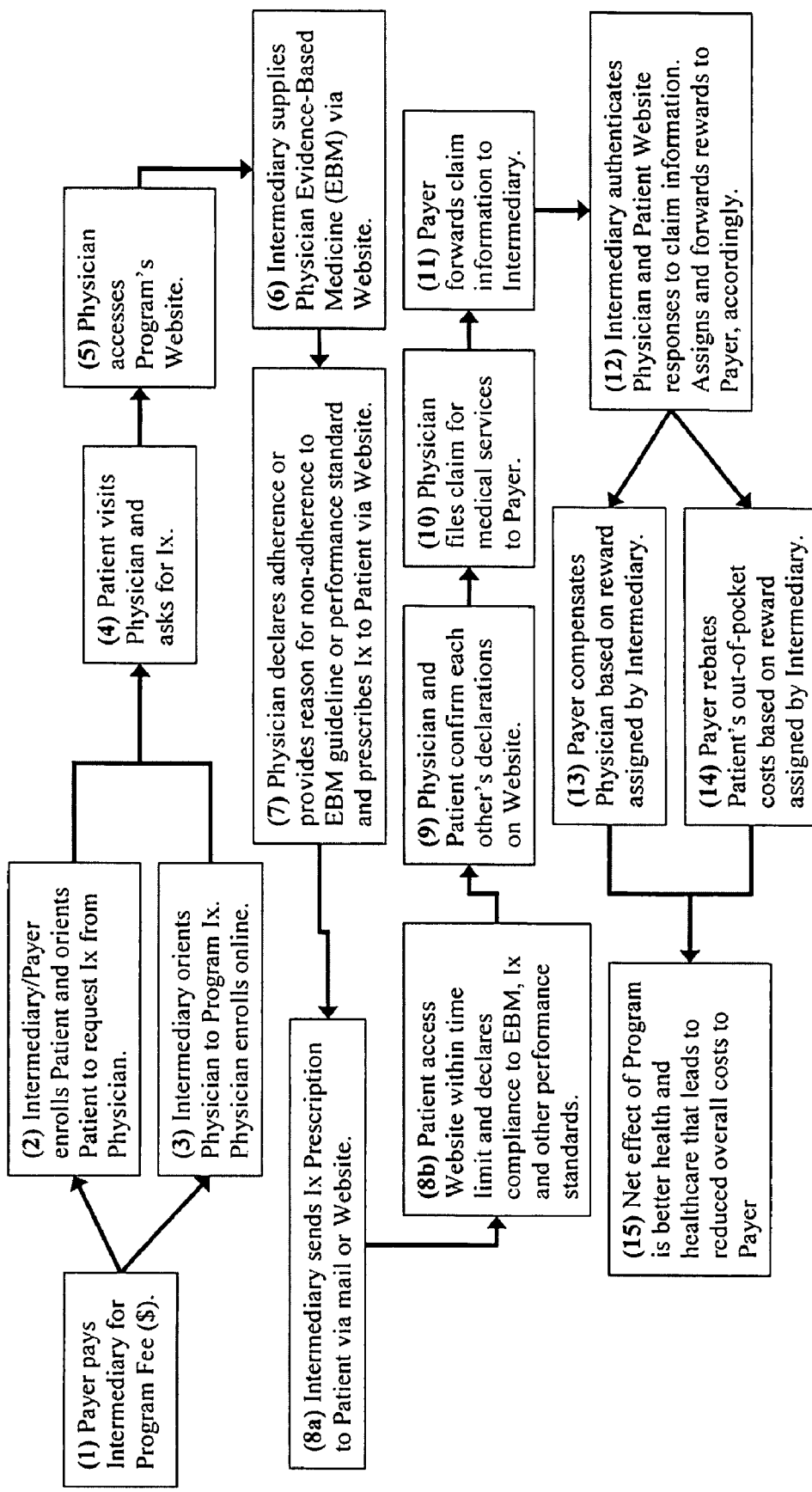
FIG. 3 is a diagrammatic illustration of an Ix Program embodiment of the method of the present invention.
Figure 10:
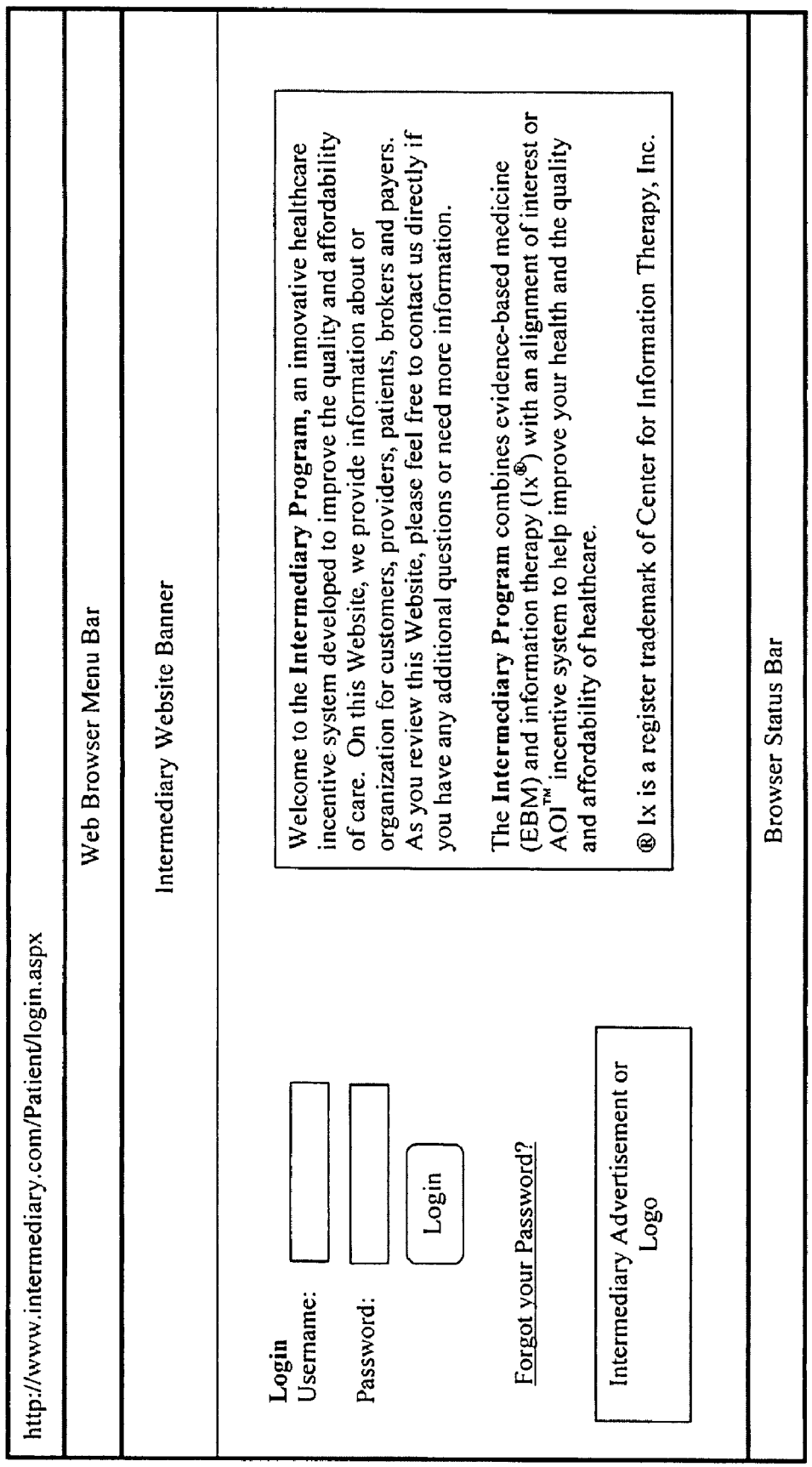
FIG. 10 shows an initial "welcome page" on a patient side of the present method.

FIG. 3 diagrammatic illustration of the method of the present invention. The embodiment of FIG. 3 comprises an Ix Program. The following discussion provides a step-by-step description is intended to provide an illustration of combining the method and system of the present invention method with the mechanics of the Ix Program process and is not intended to imply that this is the only application of the invention. The following discussion is made in reference to FIGS. 3-13. FIG. 3 illustrates the steps of the process described below. FIG. 4-13 provide exemplary webpage interfaces useful with the present invention.

The example of the present invention discussed below comprises a web-based healthcare delivery incentive method (system or program) that, in this example, is referred to as the Ix Program (Program). The Program described herein involves four parties: health care purchasers and payers (health insurance companies, self-insured employers and the Medicare and Medicaid programs) that purchase the Program and underwrite (fund) the cost of health care of persons (beneficiaries) covered by health insurance (health plan); medical providers (service providers, physicians/doctors and hospitals) who participate in the Program; beneficiaries (patients/consumers) of a purchaser/payer's health plan that offers the Program; and an intermediary (Informediary) that operates the Program.

The current invention comprises the following elements: a performance standard or set of performance standards; an Internet application; financial rewards; and a system of checks and balances. The performance standards may comprise a set of care and treatment standards that have been shown to be effective at improving health care rendered by providers, improving the health of beneficiaries, and controlling health care costs such as evidence-based medicine (EBM) treatments and information therapy (Ix) prescriptions. The Website contains the Program's proprietary applications and performance standards or information about performance standards operated by the intermediary. The financial rewards and other types of non-financial incentives are disbursed by the purchaser/payer to providers and beneficiaries for successfully practicing the Program as determined by the intermediary. The system of checks and balances is established between the provider and beneficiary to motivate Program participation and performance standard compliance, and to prevent fraud and abuse.

With reference now to FIG. 3, at Step #1 the payers/purchasers adopt the program by purchasing the Program from the intermediary (labeled as Medencentive in FIG. 3) as a "bolt-on" benefit to the purchaser/payer's health plan. Typically, payment for a "bolt-on" benefit is made on the basis of the number of plan members (consumers/patients) who are covered by the Program, often referred to as a per-member-per-month (PMPM) access fee.

At Step #2 the beneficiaries enroll, receive orientation and are encouraged to request information therapy from service providers. Beneficiaries may be introduced to and enrolled in the Program through their employment or health insurer. The intermediary and the purchaser/payer orient beneficiaries (patients) to the Program through written materials, instructional videos, and Website tutorials. One instruction advises beneficiaries to seek care from a participating provider or to encourage their physician to participate in the Program. Beneficiaries should expect to receive care from his/her provider that meets the performance standard such as EBM treatments and information therapy prescriptions. The Program orientation explains that financial rewards are available to the beneficiary when he/she appropriately responds on-line (or over the telephone) to information therapy prescribed by his/her physician and/or meets other performance standards through the Program's Website or by telephone.

At Step #3 the service providers (physicians) receive orientation and are encouraged to prescribe Ix. Physicians may be introduced to the Program in a variety of ways including organized meetings, in-office presentations, mailings, through professional organizations, and faxed notices from the intermediary. Another common means of introduction may include patients requesting that their physicians participate in the Program and provide the performance standard service such as information therapy. Similar to the beneficiary, the intermediary or health plan orients physicians through written materials, instructional videos, and Website tutorials. The provider is informed that by practicing the Program, he/she: 1) should have more compliant and knowledgeable patients, 2) will be rendering a higher standard of care, 3) may gain a degree of malpractice risk management, 4) should experience a gain in productivity, 5) should expect a better clinical outcome, and 6) will be appropriately compensated for his/her time and effort. The provider is also informed that the patient will be seeking and expecting information therapy, EBM treatments, and/or other performance standards, and that the patient will be asked to rate the physician's level adherence to the performance standard. Finally, providers are informed that participation is designed to be fast and easy through the Program's Website. Physicians enroll in the Program online through the Website.

At Step #4 the beneficiary visits a physician and asks for information therapy and/or other performance standards. When the beneficiary seeks a provider participating in the Program or requests services that satisfy the Program's performance standard(s) from his/her physician, it represents the first in a series of checks and balances (non-financial or psychological incentives) between these parties that encourages positive behavior modification. During an office visit (or other types of medial encounter), the physician renders EBM treatments to the patient and files a normal insurance claim to the purchaser/payer for compensation. The physician would collection any co-payments or annual deductibles from the patient according to the patient's health plan benefits.

Continuing with Step #5 the physician accesses the program through the Program's Website. The physician can practice the Program in many ways. Two exemplary methods of practicing the present invention are discussed herein. The physician can initiate the process at the time of service (in the presence of the patient or shortly thereafter) by accessing the intermediary's Website and using the Point of Service Initiated or POSI™ real-time version of the Program (FIG. 4). On the Website, the physician enters the beneficiary's name or identification number and diagnosis(es) (See FIGS. 5, 6 and 7) and responds to questions and/or performs services at Step #7, as described below. The physician's POSI responses are stored in the Website's database for later processing. If the physician forgets or fails to use POSI, then the process can be performed "after-the-fact" using the Claims Initiated or CT Version of the Program. The Website's proprietary software applications determine whether the POST or the CI version is to be used for each occurrence of care. This is accomplished when the intermediary receives (preferably electronically) a copy of the physician's insurance claim from the health plan (as mentioned in Step #4, above, and described in Step #10 below). The Website's software applications look to match the claim Information to POSI responses by the physician stored in the Website's database. If there is a match, then the intermediary orders compensation for the physician as described in Step #12, below. If there is no match, then the intermediary sends an e-mail notification to the physician to practice the Program "after-the-fact." This "after-the-fact" process that uses a physician's insurance claim to initiate an e-mail notification to the physician, in effect, is the Claims Initiated or CI version of the Program. The CI version is not depicted in the diagram. However, with the exception of how the processes are initiated, the POSI and CI versions are the same.

At Step #6 the Program Website supplies EBM treatment guidelines or other types of performance standards. The Website automatically displays EBM treatment guidelines or other types of performance standards to the physician related to the patient's diagnosis(es) and/or health plan benefits. In the case of the Ix Program, if a guideline does not exist, then the Website displays medical content related to patient's diagnosis(es) (FIG. 8).

Other types of performance standards include but are not limited by: web-based patient-integrated pre-authorization certification of expensive medical services; web-based patient-integrated hospital care management services; web-based drug therapy and pharmacy benefit management programs including e-prescription, therapeutic drug substitution, and automated drug interaction warnings; the adoption and use of personal health records; web-based health risk assessment programs; web-enabled health screening programs; web-enabled disease management programs; web-based medical education programs; web-enabled wellness and fitness programs; web-enabled health monitoring devices; promotion of web-based patient health self-management programs; and or other programs and systems shown or designed to improve the standard of care, promote healthiness and control costs or make health care more affordable.

In Step #7 the physician responds to Website questions designed to initiate an Ix Prescription to the Patient. In the case of the Ix Program model of the invention, if a guideline is displayed on the Website (FIG. 8), the physician is asked to answer three questions:

a. "Are you following this guideline for this patient? Yes or No"

A physician's answer to this single question has a profound affect on how health care is delivered as a result of the method (invention). In effect, the physician is aware that his/her patient will be asked later in the process to read the same guideline information. The patient will be tested to demonstrate his/her knowledge of the guideline. Then the patient will be asked to rate the physician's performance or adherence relative to the guideline. This process of the physician declaring adherence to a guideline (or any type of performance standard presented on the Website) and a "knowledgeable" patient subsequently confirming or refuting the physician's declaration of adherence is one of the most powerful checks and balances of the method (invention). It is obviously intended to encourage physicians to be adherent to EBM guidelines (or other performance standards) and for patients to be knowledgeable and discriminating about the health they receive. In effect, the purchaser/payer is compensating both the physician and patient to participate in this check and balance with the expectation that better health care will rendered, and that this will lead to better health and lower costs. It is important to note that one of the most important aspects of the method (invention), which makes it especially attractive to physicians, is its "anti-cookbook medicine" feature. This feature allows physicians to answer this guideline adherence question either "yes" or "no," and still earn full compensation for practicing the method. The reason payers/purchasers would agree to pay physicians when they answer this question "no" is because the method requires physicians to select a reason for non-adherence to a guideline from a popup menu (refer to FIG. 9). The physician's reason for non-adherence is stored in the Website's database to be presented to the patient later in the process. The payer/purchaser knows that physician is aware that his/her reason for deviation will be judged by an informed patient. This check and balance solves the issue physicians have had with "cookbook medicine" associated with other pay-for-performance methods that forces them to follow a protocol or guideline to be compensated. In fact this feature encourages physicians to answer "no" when it is appropriate so that the patient is educated why a guideline does not fit his/her particular health condition.

b. "Do you wish to prescribe information therapy to this patient? Yes or No"

Most payer/purchasers will require physicians to answer "yes" to this question or indicate why the information should not be prescribed to the patient or indicate that he/she has provided other information to the patient. In the latter case, the patient will be queried later in the process about the information supplied by the physician or for the patient to express an opinion about the physician's decision to not prescribe information through the Website. It should also be noted that this act of prescribing information therapy is extra effort exerted by the physician, which supports the case for additional pay. (Note: Many payers/purchasers are not enthusiastic about pay-for-performance program that compensate physicians more for merely following a recommended treatment guideline because payers/purchasers feel this is what the physician is being paid to do in the first place. This is not the case in the Program's method.)

c. "Please rate your patient's compliance for this diagnosis: Compliant, Compliance is a non-factor, or No response"

This is an optional question that a payer/purchaser can elect to have added to the Program. Typically, purchaser/payers will assign a portion of the patient's financial reward based on how the physician answers this question. Response to this question is not made available to the patient to prevent undermining doctor-patient relations.

Once the physician answers these questions, the POSI real-time version of the Ix Program model allows the physician to print an "information therapy prescription" to hand to the patient before the patient leaves the office. Alternatively, the physician can practice the real-time version at the end of the day for all enrolled beneficiaries and the intermediary will mail or e-mail the prescriptions to each patient. (In the CI after-the-fact version, all Ix prescription letters may be sent by mail or e-mail.) The process continues for the physician when he or she is asked to review and consider patient responses to the Website's questionnaires. These responses are available to the physician through the Website. Responses that indicate the patient is experiencing additional medical issue or distress is sent to the physician as a priority e-mail notice. Since physician participation in the Program is voluntary on a per-occurrence-of-care basis, the act participation by a physician is an indication that the physician is committed to delivering a higher standard of care, is committed to better patient communication, is interested in patient compliance to recommended treatments, and is willing to have his/her performance judged by his/her patient. Conversely, a physician's non-participation may imply a whole other set of values that may result in patient and purchaser/payer dissatisfaction.

The Physicians' level of participation and patient ratings will be aggregated over time. These results will typically be first made available to physician peer review organizations to provide a degree of due process. Eventually these results are made available to purchaser/payers and the general public, thus allowing market forces to provide additional motivation (incentive). But, perhaps the most powerful incentive is that physicians simply do not want their patients to think they practice inferior medicine.

In other models of the invention, other types of performance standards can and will be accommodated. However, the process of the provider (physicians and hospitals) being asked to demonstrate or declare adherence to a given performance standard, followed by the patient being asked to learn and demonstration knowledge about the performance standard, and once qualified, the patient being asked to rate the provider's performance against the standard remains the same for all types of performance standards. The process step of physicians rating their patients' adherence to recommended care and the process step of physicians having access to their patients' Website responses (including medical issue warnings) also remain the same for all types of performance standards. The invention is most effectively delivered through the Internet, though it can be delivered by telephone or other means, provided that the parties and the other elements of the invention remain the same as described herein.

At Step #8 of the present invention the patient receives and responds to the Ix Prescription on the Website. In the Ix Program model of the invention, the patient receives his/her information therapy (Ix) prescription letter from his/her physician as he/she leaves the physician's office or by mail or e-mail. The prescription letter directs the patient to access the Program's Website (See FIG. 10) where his/her actual prescription will be ready and waiting as a result of the physician's earlier responses to the Website. For each diagnosis entered by the physician associated with this occurrence of care, the beneficiary is asked to do the following on the Website to earn his/her financial reward:

1. Read the health information about his/her diagnosis including EBM treatments, recommended care, health maintenance, and/or other performance standards (refer to FIG. 11);
2. Answer a questionnaire indicating his/her knowledge or understanding of the health information (refer to FIG. 12);
3. Answer a questionnaire about his/her compliance to the recommended care;
4. Answer a questionnaire to rate his/her physician's performance against EBM treatments, recommended care, or other performance standards;
5. Review any reasons recorded by the physician for non-adherence to the treatment guideline or other performance standard and answer a questionnaire to express a qualified opinion in regards to the physician's reason for non-adherence;
6. Alternatively, elect to authorize the release of the physician's rating of his/her compliance to recommended care (if the physician is asked this question); and
7. Authorize the release of his/her responses to the questionnaires to his/her physician (excluding the patient's rating of the physician's performance and any opinions expressed about reasons for deviating from a guideline).

As the patient answers these questions, he/she scores points toward a financial reward for this occurrence of care. Once his/her point total reaches a required threshold, the Website presents a voucher (See FIG. 13) that notifies the patient that he/she has earned the financial reward offered by his/her purchaser/payer. Similar to the physician, patient participation in the Program is voluntary on a per-occurrence-of-care basis. The act of accessing the website and responding appropriately to the questions is an indication that the patient is motivated to maintain or improve his/her health.

The patient's participation and authorization to release his/her responses to the questionnaires to his/her physician is an indication that the patient wants his/her physician to know he/she understands his/her medical condition and is committed to being compliant to recommended care and healthy behavior. In the process, the patient learns valuable information that he/she may have not known or did not understand or forgot to ask the physician that can be used to better self-manage his/her health. In addition, the patient gains the peace of mind that he/she is receiving EBM treatments or other standard of performance from his/her physician. Finally, the patient receives a financial reward for his/her effort and healthy behavior.

As with service providers (physicians and hospitals), other types of performance standards can and will be accommodated. However, the process of the provider (physicians and hospitals) being asked to demonstrate or declare adherence to a given performance standard, followed by the patient being asked to learn and demonstration knowledge about the performance standard, and once qualified, the patient being asked to rate the provider's performance against the standard remains the same for all types of performance standards. The optional process step of physicians rating their patients' adherence to recommended care and the process step of physicians having access to their patients' Website responses (including medical issue warnings) also remain the same for all types of performance standards.

In Step #9 the physician and patient confirm each other's performance using the Internet application. As mentioned in reference to Steps #7 and #8, the method asks the physician and patient to review and confirm each other's declarations of compliance to an EBM benchmark and/or other performance standards. Both parties are aware that this confirmation is built into the process as a requirement to earn the financial rewards. Physicians do not want their patients to think they practice inferior medicine. Conversely, patients (especially patients with chronic conditions that have close relationships with their physicians) generally do not want to disappoint their physicians by not being compliant. As a result physicians (and hospitals) and patients are motivated to adopt behaviors that improve health care and healthiness. Furthermore, since both parties are aware that their responses are being recorded and stored by an independent third party (the intermediary), and that this information could be reported to purchasers/payers and the general public to identify preferred providers. In effect, the method's process that combine financial and non-financial rewards (and potential penalties) creates powerful "checks and balances" that encourages a higher standard of care and healthier behavior that leads to lower costs.

At Step #10 the physician files a health insurance claim with the Payer/Purchaser. As mentioned with reference to Steps #4 and #5, the normal filing of an insurance claim by the physician for medical services covered by the Program can occur before, concurrently, or after the method is practiced by the physician. (An insurance claim contains all the information needed by the Program's web-based applications to complete the process.) The claim must be filed within a certain time limit established by the payer/purchaser and the intermediary. If a physician does not access the Website and practiced the POSI real-time version of the method by the time the physician's claim reaches the intermediary, then the CI afterthe-fact version of the method will send an e-mail notification to the physician. This is referred to as a "CI opportunity." The physician will have a time limit to respond to a "CI opportunities." If a "CI opportunity" expires, the purchaser/payer and intermediary may elect to send the patient an Ix prescription based on the diagnosis(es) listed on the insurance claim submitted by the physician. This allows patients to gain valuable health information and earn a financial reward, even when their physicians fail to participate in the Program. This process is referred to as "system-generated information therapy." To encourage physician participation while insuring patients are not deny the opportunity to participate in the Program when their physician fail/forget to participate, the purchaser/payer and intermediary can offer patients larger financial rewards for "physician-generated Ix" than for "system-generated Ix."

Step #11 comprises the payer/purchaser sending claim 1nformation to the intermediary. The purchaser/payer forwards all insurance claims to the intermediary. Preferably, claims are sent automatically and electronically on a daily basis, using industry standard electronic data interchange (EDI) interfaces and formats. Once downloaded into the intermediary's computer, the Website software applications sort the data to find claims containing covered medical services rendered to covered beneficiaries.

Step #12 comprises the intermediary adjudicates claims, authenticates physician and patient responses, and directs financial compensation and other rewards. As described with reference Step #5, above, the intermediary uses the Website's software applications to match insurance claims to physician POSI responses stored in the Website's database. If there is a match, the intermediary sends an (electronic) authorization/directive to the purchaser/payer to compensate the physician (and sends the information therapy prescription to the patient as described in Step #7, above). Since the POSI real-time version is the preferred method, the intermediary can select a premium or highest rate of compensation for the physician. If the intermediary cannot match an applicable insurance claim to a POSI, then the Claim 1nitiated or CI version of the method sends an e-mail notification to the physician. If the physician responds to the "CI Opportunity" and successfully practices the method within the allotted time, then the intermediary sends an (electronic) authorization/directive to the purchaser/payer to compensate the physician (and sends the information therapy prescription to the patient as described in Step #7, above). Since the POSI real-time version is the preferred method, the intermediary can select a lower rate of compensation for the physician practicing the CI after-the-fact version of the method. The Website applications track patient information therapy and other performance standards responses. When a patient successfully completes a prescription or other performance standard through the Website (or over the telephone or by other means), then the Website's applications adjudicate the patient's reward and the intermediary sends an authorization/directive to the payer/purchaser to pay the assigned reward to the patient. If the physician or the patient do not independently and individually (or perhaps dependently and collectively) respond to their respective Program "opportunities" within established timeframes, then the Website applications close-out each opportunity accordingly, and the physician and patient do not earn financial compensation or rewards. All of these events are recorded and stored for future consideration by the intermediary and the payer/purchaser.

Step #13 comprises the payer/purchaser compensating the physician. When the payer/purchaser receives the payment authorization/directive from the intermediary, the purchaser/payer reimburses the physician one of multiple levels of compensation according to the contracted terms between the payer/purchaser or intermediary and the physician. Alternatively, the purchaser/payer may assign the payment function to the intermediary. In this case, the intermediary makes payments to physicians from funds supplied by the purchaser/payer. In the present invention and under the terms of the agreement between the purchase/payer or intermediary and the service provider, variety amounts of compensation can be paid for a variety of performances standards.

At Step #14 the payer/purchaser pays the beneficiary a financial reward. When the payer/purchaser receives the payment authorization/directive from the intermediary, the purchaser/payer pays the patient one of multiple levels of compensation according to the purchaser/payer's health plan and the performance standard achieved by the patient. Alternatively, the purchaser/payer may assign the payment function to the intermediary. In this case, the intermediary makes payments to patient from funds supplied by the purchaser/payer.

Step #15 comprises the payer/purchaser realizing a cost savings. Though this is not an actual step in the process, the intended by-products of the method is a higher standard of care (featuring EBM treatments and information therapy) and healthier behavior that studies have shown leads to lower costs. In the current invention, the purchaser/payer agrees to compensate medical providers and patients to "declare and confirm" their adherence to performance standards, and to compensate the intermediary for operating the system and authenticating physicians and patients' declarations and confirmations. More specifically, the purchaser/payer agrees, in order to achieve better health and health care that leads to cost containment and greater value, to:

a. compensate the medical provider (physician and hospital) for:
   1. declaring adherence to (or demonstrating the rendering of) evidence-based treatments and other performance standards;
   2. having their patients express a qualified opinion or rating of their (the physician's) performance or adherence to EBM treatments;
   3. rating their patients' level of adherence to recommended care; and
   4. responding to their patients' responses to the Website's questionnaires and inputs to include warnings of medical issues;

b. financially reward patients (beneficiaries) for:
   1. seeking evidence-based and performance standard health care from medical providers;
   2. learning how to self-manage their health, including taking tests to certify their knowledge;
   3. declaring adherence to healthy behaviors and other related performance standards;
   4. rating their medical providers' adherence to evidence-based treatments and other performance standards;
   5. recording their health status; and
   6. agreeing to allow their medical providers to review their responses and rate their adherence to desired performance standards; and c. compensate the intermediary for:
   1. operating the invention's incentive system to include the Program's Website and/or other technologies;
   2. developing and maintaining the associated software applications and databases;
   3. providing and/or interfacing the performance standards;

4. adjudicating and authenticating medical providers and patients' declarations, confirmations, demonstrations, and acknowledgments of adherence to performance standards;
5. directing and/or affecting service provider and patient compensation and financial rewards;
6. tracking, reporting, and analyzing results; and
7. recommending refinements to the Program to include "precision guided incentives and performance standards" (adjustments to and expansion of the incentives and performance standards).

By combining the parties and elements of the method in the manner describe herein, the invention "triangulates" the interests of healthcare's key stakeholders—the purchaser/payer, the medical provider and the consumer/patient—in a win-win-win proposition. By attaining this unique "triangulation" among these key stakeholders, the invention achieves the goals of better health and better and more affordable health care. Thus the invention can be described as a "web-based healthcare incentive system" that creates an "alignment of interests" among the key stakeholders to achieve the goals of better health and better and more affordable health care. As a result, the invention is better described as an "alignment of interest" or "AOL" program as opposed to the more familiar pay-for-performance program descriptor.

Other embodiments of the current invention will be apparent to those skilled in the art from a consideration of this specification or practice of the invention disclosed herein. However, the foregoing specification is considered merely exemplary of the current invention with the true scope and spirit of the invention being indicated by the following claims.

What is claimed is:

1. A method for managing delivery of healthcare services using a web-based or telephonic system interface, the method comprising:

receiving a diagnosed health condition of a patient and a claim for services rendered from a service provider at a computer system comprising a processor programmed to process the diagnosed health condition and send a service provider performance standard and a patient performance standard to the service provider based on the received diagnosed health condition;

transmitting, from the computer system, an offer of a performance-based reward to the service provider for demonstrating or declaring adherence or for providing a reason for non-adherence to the service provider performance standard, for agreeing to allow the patient to confirm or acknowledge the service provider adherence or reason for non-adherence to the service provider performance standards, and for prescribing to the patient the patient performance standard through the web-based or telephonic interface;

transmitting, from the computer system, a notification to the service provider that the patient will receive an offer of a performance-based reward for demonstrating or declaring adherence or a reason for non-adherence to the patient performance standard prescribed by the service provider, and that the service provider must acknowledge the offer of a performance-based reward to the patient to receive the service provider performance-based reward;

transmitting a query from the computer system to the service provider to generate a service provider declaration of adherence or a service provider reason for non-adherence to the service provider performance standard and a service provider agreement to allow the patient to acknowledge or confirm the service provider declaration of adherence or the service provider reason for non-adherence to the service provider performance standard, to generate an acknowledgment from the service provider that the patient will be offered a performance-based reward for demonstrating or declaring adherence or providing a reason for non-adherence to the patient performance standard prescribed by the physician, to generate a service provider prescription of the patient performance standard, and to generate a service provider agreement to confirm or acknowledge a declaration of patient adherence or a reason for non-adherence to the patient performance standard;

receiving at the computer system the service provider declaration of adherence or the service provider reason for non-adherence to the service provider performance standard, the service provider agreement to allow the patient to acknowledge or confirm the service provider declaration of adherence or the service provider reason for non-adherence to the service provider performance standard, the service provider acknowledgment that the patient will receive the performance-based reward after the patient declares adherence or provides a reason for non-adherence to the patient performance standard, the service provider prescription of the patient performance standard, and the service provider agreement to confirm or acknowledge the declaration of patient adherence or the reason for non-adherence to the prescribed patient performance standard;

transmitting to the patient from the computer system an offer of a performance-based reward to the patient for demonstrating or declaring adherence or for providing a reason for non-adherence to the patient performance standard, for agreeing to allow the service provider to confirm or acknowledge the patient adherence or reason for non-adherence to the patient performance standard, and for confirming or acknowledging the service provider adherence or reason for non-adherence to the service provider performance standard, through the web-based or telephonic interface, based on the service provider prescription of the patient performance standard or the diagnosed health condition of the patient or the claim for services rendered submitted by the service provider;

transmitting from the computer to the patient the diagnosed health condition, the service provider performance standard, the service provider declaration of adherence or the service provider reason for non-adherence to the service provider performance standard, and the patient performance standard prescribed by the service provider or, if the service provider does prescribe a patient performance standard, a patient performance standard generated by the computer system based on the on the diagnosed health condition of the patient or the claim for services rendered submitted by the service provider;

transmitting a query from the computer to the patient to generate a patient demonstration of knowledge of the diagnosed health condition, a patient declaration of patient adherence or patient reason for non-adherence to the patient performance standard, and a patient agreement to allow the service provider to acknowledge or confirm the patient demonstration of knowledge of the diagnosed health condition and the declaration of patient adherence or patient reason for non-adherence to the patient performance standard;

receiving and processing at the computer system the patient demonstration of knowledge of the diagnosed health condition, the patient declaration of adherence or the patient reason for non-adherence to the patient performance standard, and the patient agreement to allow the service provider to acknowledge or confirm the patient demonstration of knowledge of the diagnosed health condition and the patient declaration of adherence or the patient reason for non-adherence to the patient performance standard;

transmitting the patient demonstration of knowledge of the diagnosed health condition and the patient declaration of adherence or the patient reason for non-adherence to the patient performance standard from the computer system to the service provider;

transmitting a query from the computer system to the service provider to generate a service provider confirmation or acknowledgment of the patient demonstration of knowledge and the patient declaration of adherence or the patient reason for non-adherence to the patient performance standard;

transmitting a query from the computer system to the patient to generate a patient confirmation or acknowledgment of the service provider declaration of adherence or the service provider reason for non-adherence to the service provider performance standard;

receiving at the computer system, and processing for authentication the service provider confirmation or acknowledgment of the patient demonstration of knowledge of the diagnosed health condition and the patient declaration of adherence or the patient reason for non-adherence to the patient performance standard, the patient confirmation or acknowledgment of the service provider declaration of adherence or the service provider reason for non-adherence to the service provider performance standard, the service provider declaration of adherence or the service provider reason for non-adherence to the service provider performance standard, and the patient declaration of knowledge of the diagnosed health condition, the patient declaration of adherence or the patient reason for non-adherence to the patient performance standard; and the computer system authorizing disbursement of a performance-based incentive to the service provider and a performance-based incentive to the patient after authentication.

2. The method of claim 1 wherein the service provider declaration of adherence comprises a demonstration of an action or physical act independently verifiable by the patient and capable of authentication by the computer system controlled by an independent intermediary and wherein the patient declaration of adherence comprises a demonstration of an action or physical act independently verifiable by the service provider and capable of authentication by the computer system controlled by an independent intermediary.

3. The method of claim 1 wherein the service provider confirmation of the patient declaration of adherence comprises an acknowledgment of a patient demonstrated act and wherein the patient confirmation of the service provider declaration of adherence comprises an acknowledgment of a service provider demonstrated act.

4. The method of claim 1 wherein the performance-based incentive to the service provider is disbursed to the service provider only after confirmation, verification or acknowledgement of the service provider declaration of adherence or service provider reason for non-adherence by the patient and wherein the performance-based incentive to the patient is disbursed to the patient only after confirmation, verification or acknowledgement of the patient declaration of adherence or patient reason for non-adherence by the service provider.

5. The method of claim 1 wherein authenticating the service provider reason for non-adherence or authenticating the patient reason for non-adherence comprises the processor automatically validating the patient or service provider reason for non-adherence and disbursing an amount of the performance-based incentive to the service provider or the patient based upon validity of the reason for non-adherence based on the confirmation or acknowledgment by the patient and service provider, respectively.

6. The method of claim 1 wherein the diagnosed health condition is received by the computer at an independent intermediary, wherein the computer at the independent intermediary comprises a processor to determines a level of adherence to the performance standard by the service provider and the patient and determines an amount of performance-based incentive for disbursement to the service provider and patient based upon the level of adherence of each, determined by the service provider and the patient agreement to allow the other party to confirm or acknowledge each other's level of adherence and the confirmation or acknowledgment of the level of adherence by the service provider and patient, respectively.

7. The method of claim 1 wherein transmitting the diagnosed health condition and performance standard to the patient comprises allowing the patient access to a website containing the patient's diagnosed health condition and the performance standard and wherein transmitting a query to the patient to generate a patient demonstration of knowledge of the diagnosed health condition and performance standard comprises providing the patient with a series of questions through the website regarding the diagnosed health condition and the performance standard and receiving a series of responses from the patient to the series of questions.

8. The method of claim 1 wherein the service provider performance standard and the patient performance standard comprises at least one member selected from a group comprising: a web-based recommended treatment guideline; a web-based information therapy consisting of patient health educational material, a web-based drug therapy prescription system, a web-based pre-authorization certification program, a web-based wellness and prevention program, a web-based health risk assessment program, a web-enabled health screening program, a web-based personal or electronic health record system, web-enabled patient health monitoring devices, a web-based medical advancement education and acknowledgment system, a web-based service provider continuing education system, and a web-based evidence-based hospital treatment plan system.

9. The method of claim 1 wherein the service provider submits the claim for services rendered to a health plan, the method further comprising:

receiving a request for authentication of the service provider confirmation, the patient confirmation, the service provider declaration of adherence or reason for non-adherence, the patient demonstration of knowledge, declaration of adherence or reason for non-adherence, the service provider agreement to allow the patient to acknowledge or confirm the service provider demonstration or declaration of adherence or the service provider reason for non-adherence to the service provider performance standard, the service provider agreement to acknowledge or confirm the patient demonstration of knowledge of the diagnosed health condition and the patient declaration of adherence or the patient reason for non-adherence to the patient performance standard, the patient agreement to allow the service provider to acknowledge or confirm the patient demonstration of knowledge of the diagnosed health condition and the declaration of patient adherence or the patient reason for non-adherence to the patient performance standard, and the patient agreement to acknowledge or confirm the service provider declaration of adherence or the service provider reason for non-adherence to the service provider performance standard;

transmitting authorization to disburse the performance-based incentive to the service provider upon authentication of the service provider declaration of adherence or reason for non-adherence and the patient confirmation of the service provider declaration of adherence, the service provider agreement to allow the patient to acknowledge or confirm the service provider demonstration or declaration of adherence or the service provider reason for non-adherence to the service provider performance standard, the service provider agreement to acknowledge or confirm the patient demonstration of knowledge of the diagnosed health condition and the patient declaration of adherence or the patient reason for non-adherence to the patient performance standard; and transmitting authorization to disburse the performance-based incentive to the patient upon authentication of the patient demonstration of knowledge, the patient declaration of adherence or authentication of the patient reason for non-adherence and the service provider confirmation of the patient demonstration of knowledge, the patient declaration of adherence, or the patient reason for non-adherence, the patient agreement to allow the service provider to acknowledge or confirm the patient demonstration of knowledge of the diagnosed health condition and the declaration of patient adherence or the patient reason for non-adherence to the patient performance standard, and the patient agreement to acknowledge or confirm the service provider declaration of adherence or the service provider reason for non-adherence to the service provider performance standard.

10. The method of claim 1 wherein the authentication and authorization steps of claim 1 are performed by an independent intermediary or health plan computer system.

11. A web-based or telephonic method for managing healthcare delivery, the method comprising:
receiving a patient identification and at least one diagnosis from a service provider through a web interface;
processing the at least one diagnosis from the service provider and automatically selecting and transmitting a service provider performance standard and a patient performance standard including patient educational material to the service provider corresponding with each diagnosis received from the service provider from a computer system through the web interface;
receiving a service provider declaration of adherence or a service provider reason for non-adherence to the service provider performance standard from the service provider;
receiving a service provider agreement to rate the patient adherence to the patient performance standard and a service provider agreement to allow the patient to rate the service provider adherence or reason for non-adherence to the service provider performance standard;
receiving a prescription from the service provider of the patient performance standard including educational material in the form of an information therapy prescription to the patient;
receiving a rating from the service provider of the patient adherence or reason for non-adherence to the patient performance standard subsequent to receiving the patient declaration of adherence or reason for non-adherence to the patient performance standard;
receiving authorization from the service provider to allow the patient to verify the service provider declaration of adherence to the performance guideline or to express an opinion about the reason for non-adherence and to have the service provider declaration of adherence to the performance standard or the service provider reason for non-adherence authenticated and adjudicated by the computer system;
receiving a patient agreement to verify the service provider declaration of adherence or reason for non-adherence to the service provider performance standard and a patient agreement to allow the service provider to rate the patient adherence or reason for non-adherence to the patient performance standard; and
automatically authorizing disbursement of a performance-based incentive to the service provider after the patient verifies the service provider declaration of adherence or the service provider reason for non-adherence and after the service provider declaration of adherence or the service provider reason for non-adherence to the service provider performance standard has been authenticated and adjudicated by the computer system.

12. The method of claim 11 wherein authorizing disbursement of a performance-based incentive to the service provider comprises:
transmitting an instruction from the computer system to a health plan to disburse the performance-based incentive comprising monetary compensation to the service provider.

13. The method of claim 11 further comprising the computer system receiving a patient declaration of adherence or a reason for non-adherence to the patient performance standard from the patient.

14. The method of claim 13 further comprising the computer system receiving a service provider confirmation of the patient declaration of adherence or a service provider confirmation of the patient reason for non-adherence to the patient performance standard.

15. The method of claim 14 comprising the computer system authorizing disbursement of the performance-based incentive to the patient after the computer system authenticates that the service provider verified the patient declaration of adherence or reason for non-adherence to the patient performance standard, and after authentication and adjudication of the patient declaration of adherence or reason for non-adherence to the patient performance standard by the computer system.

16. The method of claim 11 wherein the computer system is administered by an independent intermediary and the diagnosis is received by the independent intermediary.

17. The method of claim 11 further comprising:
allowing the patient access to a website containing the diagnosis and the patient performance standard;
assessing patient knowledge of the diagnosis and the patient performance standard by using the website to present the patient with at least one question regarding the diagnosis and the patient performance standard; and
wherein the computer system receives at least one response from the patient to the at least one question.

18. The method of claim 11 wherein the service provider further submits to a health plan a claim for services rendered, the method further comprising:

receiving a request for authentication of the service provider declaration of adherence or the service provider reason for non-adherence;

transmitting authorization to the health plan to disburse the performance-based incentive to the service provider, wherein said authorization is transmitted from the computer system administered by an independent intermediary to the health plan after authentication of the service provider declaration of adherence or the service provider reason for non-adherence, and the patient confirmation of the service provider declaration of adherence or service provider reason for non-adherence.

19. A web-based or telephonic system for managing healthcare delivery, the system comprising:

a healthcare services provider web-based or telephonic interface comprising a plurality of data fields to accept a patient identification and a medical diagnosis of the patient from a healthcare services provider, to communicate an offer of a performance-based reward to the healthcare services provider for demonstrating or declaring adherence or for providing a reason for non-adherence to the healthcare services provider performance standard, for agreeing to allow the patient to confirm or acknowledge the healthcare services provider adherence or reason for non-adherence to the service provider performance standards, a notification to the healthcare services provider that the patient will receive an offered of a performance-based reward for demonstrating or declaring adherence or a reason for non-adherence to the patient performance standard prescribed by the healthcare services provider, and that the healthcare services provider must acknowledge the offer of a performance-based reward to the patient to receive the healthcare services provider performance-based reward, and for prescribing to the patient the patient performance standard through the web-based or telephonic interface, performance standard and a patient performance standard to include educational material in the form of information therapy to the healthcare services provider corresponding to the medical diagnosis, to accept a healthcare services provider declaration of adherence or reason for non-adherence to the healthcare services provider performance standard, to accept a healthcare services provider agreement to allow the patient to acknowledge or confirm the healthcare services provider declaration of adherence or reason for non-adherence to the healthcare services provider performance standard, to accept a healthcare services provider prescription of a patient performance standard, and to generate a healthcare services provider agreement to confirm or acknowledge a declaration of patient adherence or a reason for non-adherence to the prescribed patient performance standards; to accept a rating of patient adherence to the patient performance standard, and the information therapy, and to accept a healthcare services provider verification of a patient declaration of adherence to the patient performance standard;

a patient web-based or telephonic interface comprising a plurality of data fields to communicate an offer of a performance-based reward to the patient for demonstrating or declaring adherence or for providing a reason for non-adherence to the patient performance standard, for agreeing to allow the healthcare services provider to confirm or acknowledge the patient adherence or reason for non-adherence to the patient performance standards through the web-based or telephonic interface, to provide the patient with the prescribed patient performance standard and the information therapy, to provide instructions to the patient to adhere to the patient performance standard or provide a reason for non-adherence and to read or view or listen to the information therapy, to provide at least one query to the patient to assess the patient knowledge of the information therapy and the adherence to the patient performance standard, to accept at least one answer from the patient to the at least one query related to assessing the knowledge of the patient to the information therapy, to accept a patient declaration of adherence or a reason for non-adherence to the patient performance standard, to accept a patient agreement to allow the healthcare services provider to acknowledge or confirm the patient declaration of adherence or reason for non-adherence to the patient performance standard, to communicate the healthcare services provider declaration of adherence or reason for non-adherence to the healthcare services provider performance standard, to accept a patient confirmation or acknowledgment of the healthcare services provider declaration of adherence or reason for non-adherence; and a means for receiving and automatically adjudicating and authenticating the healthcare services provider declaration of adherence, the patient declaration of adherence, the patient verification of the healthcare services provider declaration of adherence, and the healthcare services provider verification of the patient declaration of adherence or reason for non-adherence; for providing an authorization for disbursement of a performance-based reward to the patient and a performance-based reward to the healthcare services provider after adjudication and authentication.

20. The system of claim 19 wherein the healthcare services provider declaration of adherence comprises an action or physical act independently verifiable by the patient and capable of authentication by the means for automatically adjudicating and authenticating and wherein the patient declaration of adherence comprises an action or physical act independently verifiable by the healthcare services provider and capable of authentication by the means for receiving and automatically adjudicating and authenticating.

21. The system of claim 20 wherein the healthcare services provider verification of the patient declaration of adherence comprises an acknowledgment of the action or physical act and wherein the patient verification of the healthcare services provider declaration of adherence comprises an acknowledgment of the action or physical act.

22. The method of claim 1 wherein the service provider must agree to allow the patient to confirm, verify, or acknowledge the service provider declaration of adherence or service provider reason for non-adherence; wherein the patient must agree to allow the service provider to confirm, verify, or acknowledge the patient declaration of adherence or patient reason for non-adherence, and wherein both the service provider and the patient further agree to allow said declarations, confirmations, verifications, or acknowledgements to be authenticated by a third party intermediary.

23. The method of claim 1 wherein the performance-based incentive to the patient is disbursed to the patient only after confirmation, verification or acknowledgement of the patient declaration of adherence or patient reason for non-adherence by the service provider.

24. The method of claim 1 wherein the performance-based incentive to the service provider is disbursed to the service provider only after confirmation, verification or acknowledgement of the service provider declaration of adherence or service provider reason for non-adherence by the patient.

\* \* \* \* \*